(12) United States Patent
Tennagels et al.

(10) Patent No.: US 7,803,571 B2
(45) Date of Patent: Sep. 28, 2010

(54) METHOD FOR IDENTIFYING IRS INHIBITORS OR AGONISTS

(75) Inventors: Norbert Tennagels, Frankfurt (DE); Jurgen Eckel, Erkath (DE); Sabine Metzger, Dusseldorf (DE); Mark Sommerfeld, Bensheim (DE)

(73) Assignee: Sanfoi-Aventis Deutschland GmbH, Frankfurt am Main (DE)

( * ) Notice: Subject to any disclaimer, the term of this patent is extended or adjusted under 35 U.S.C. 154(b) by 550 days.

(21) Appl. No.: 10/918,015

(22) Filed: Aug. 13, 2004

(65) Prior Publication Data

US 2005/0106653 A1    May 19, 2005

Related U.S. Application Data

(60) Provisional application No. 60/535,139, filed on Jan. 8, 2004.

(30) Foreign Application Priority Data

Aug. 16, 2003    (EP) .................................. 03018517

(51) Int. Cl.
C07K 7/02       (2006.01)
C07K 14/71      (2006.01)
C12Q 1/00       (2006.01)
C12Q 1/48       (2006.01)
A61K 38/00      (2006.01)
A61K 31/545     (2006.01)

(52) U.S. Cl. .......................... 435/15; 435/7.1; 435/7.2; 435/183; 514/2

(58) Field of Classification Search ........................ None
See application file for complete search history.

(56) References Cited

U.S. PATENT DOCUMENTS 5,621,075 A     4/1997  Kahn et al.
6,511,811 B1 *  1/2003  Olefsky et al. ............... 435/7.1

FOREIGN PATENT DOCUMENTS

WO    WO 98/24362    6/1998
WO    02/083730      10/2002

OTHER PUBLICATIONS

Sun XJ, Rothenberg P, Kahn CR, Backer JM, Araki E, Wilden PA, Cahill DA, Goldstein BJ, White MF, Structure of the insulin receptor substrate IRS-1 defines a unique signal transduction protein, Nature, 1991, 352, 73-77.*
Gao Z, Zuberi A, Quon MJ, Dong Z, Ye J, Aspirin Inhibits Serine Phosphorylation of Insulin Receptor Substrate 1 in Tumor Necrosis Factor-treated Cells through Targeting Multiple Serine Kinases, Journal of Biological Chemistry, Jul. 4, 2003, 287(27): 24944-24950.*
Aguirre, Vincent et al., Phosphorylation of Ser307 in Insulin Receptor Substrate-1 Blocks Interactions with the Insulin Receptor and Inhibits Insuling Action, The Journal of Biological Chemistry, (2002), vol. 277, No. 2, pp. 1531-1537.
Alessi, Dario R. et al., Mechanism of activation and function of protein kinase B, Current Opinion in Genetics & Development, (1998), vol. 8, pp. 55-62.
Backer, Jonathan M. et al., Phosphatidylinositol 3'-kinase is activated by association with IRS-1 during insulin stimulation, The EMBO Journal, (1992), vol. 11, No. 9, pp. 3469-3479.
Bandyopadhyay, Gautam et al., Glucose Activates Protein Kinase C-Zeta/Lambda through Proline-rich Tyrosine Kinase-2, Extracellular Signal-regulated Kinase, and Phosphlipase D, The Journal of Biological Chemistry, (2001), vol. 276, No. 38, pp. 35537-35545.
Bandyopadhyay, Gautam et al., PKC-Zeta Mediates Insulin Effects on Glucose Transport in Cultured Preadipocyte-Derived Human Adipocytes, The Journal of Clinical Endocrinology and Metabolism, (2002), vol. 87, No. 2, pp. 716-723.
Birnbaum, Morris J., Turning down insuling signalling, The Journal Of Clinical Investigation, (2001), vol. 108, pp. 655-659.
Braiman, Liora et al., Activation of Protein Kinase C Zeta Induces Serine Phosphorylation of VAMP2 in the GLUT4 Compartment and Increases Glucose Transport in Skeletal Muscle, Molecular and Cellular Biology, (2001), vol. 21, No. 22, pp. 7852-7861.
Burant, Charles F. et al., Phosphorylation of Insulin Receptors Solubilized from Rat Skeletal Muscle, Diabetes, (1984), vol. 33, pp. 704-708.
Cheatham, Bentley et al., Insulin Action and the Insulin Signaling Network, Endocrine Reviews, (1995), vol. 16, No. 2, pp. 117-142.
De Fea, Kathryn et al., Modulation of Insulin Receptor Substrate-1 Tyrosine Phosphorylation and Function by Mitogen-activated Protein Kinase, The Journal of Biological Chemistry, (1997), vol. 272, No. 50, pp. 31400-31406.
DeFea, Kathryn et al., Protein Kinase C Modulation of Insulin Receptor Substrate-1 Tyrosine Phosphorylation Requires Serine 612, Biochemistry, (1997), vol. 36, pp. 12939-12947.
Eldar-Finkelman, Hagit et al., Phosphorylation of insulin receptor substrate 1 by glycogen synthase kinase 3 impairs insulin action, Proc. Natl. Acad. Sci. USA, (1997), vol. 94, pp. 9660-9664.
Eriksson, Hans et al., Evidence for the key role of the adipocyte cGMP-inhibited cAMP phosphodiesterase in the antilipolytic action of insulin, Biochimica et Biophysica Acta, (1995), Vo.. 1266, pp. 101-107.
Esposito, Diana L. et al., Tyr612 and Tyr632 in Human Insulin Receptor Substrate-1 Are Important for Full Activation of Insulin-Stimulated Phosphatidylinositol 3-Kinase Activity and Translocation of GLUT4 in Adipose Cells, Endocrinology, (2001), vol. 142, No. 7, pp. 2833-2840.
Freund, Gregory G. et al., The PI3-Kinase Serine Kinase Phosphorylates Its p85 Subunit and IRS-1 in P13-Kinase/IRS-1 Complexes, Biochemical and Biophysical Research Communications, (1995), vol. 206, No. 1, pp. 272-278.

(Continued)

Primary Examiner—Julie Ha

(57) ABSTRACT

The present invention relates to a method for the identification of an IRS protein kinase inhibitor, comprising the steps of a) bringing into contact PKC-ζ with at least one IRS peptide comprising at least one PKC-ζ-Ser-phosphorylation site in the presence of at least one possible inhibitor, and b) measuring the phosphorylation of the PKC-ζ-Ser-phosphorylation site.

6 Claims, 10 Drawing Sheets

OTHER PUBLICATIONS

Gao, Zhanguo et al., Serine Phosphorylation of Insulin Receptor Substrate 1 by Inhibitor kB Kinase Complex, The Journal of Biological Chemistry, (2002), vol. 277, No. 50, pp. 48115-48121.

Greene, Michael W. et al., Positive and Negative Regulatory Role of Insuling Receptor Substrate 1 and 2 (IRS-1 and IRS-2) Serine/Threonine Phosphorylation, Biochemistry, (2002), vol. 41, pp. 7082-7091.

Hotamisligil, Gokhan S. et al., IRS-1-Mediated Inhibition of Insulin Receptor Tyrosine Kinase Activity in TNG-Alpha-and Obesity-Induced Insulin Resistance, Science, (1996), vol. 271, pp. 665-668.

Jakobsen, Soren N. et al., 5'-AMP-activated Protein Kinase Phosphorylates IRS-1 on Ser-789 in Mouse C2C12 Myotubes in Response to 5-Aminoimidazole-4-carboxamide Riboside, The Journal of Biological Chemistry, (2001), vol. 276, No. 50, pp. 46912-46916.

Kitamura, Tadahiro et al., Insulin-Induced Phosphorylation and Activation of Cyclic Nucleotide Phosphodiesterase 38 by the Serine-Theonine Kinase Akt, Molecular and Cellular Biology, (1999), vol. 19, No. 9, pp. 6286-6296.

Ladbury, John E. et al., Measurement of the binding of tyrosyl phosphopeptides to SH2 domains: A reappraisal, Proc. Natl. Acad. Sci. USA, (1995), vol. 92, pp. 3199-3203.

Lawlor, Margaret A. et al., PKB/Akt: a key mediator of cell proliferation, survival and insulin responses?, Journal of Cell Science, (2001), vol. 114, pp. 2903-2910.

Lee, Yong Hee et al., c-Jun N-terminal Kinase (JNK) Mediates Feedback Inhibition of the Insulin Signaling Cascade, The Journal of Biological Chemistry, (2003), vol. 278, No. 5, pp. 2896-2902.

Li, Jinping et al., Modulation of Insulin Receptor Substrate-1 Tyrosine Phosphorylation by an Akt/Phosphatidylinositol 3-Kinase Pathway, The Journal of Biological Chemistry, (1999), vol. 274, No. 14, pp. 9351-9356.

Liu, Van-Fang et al., Insulin Stimulates PKC Zeta-Mediated Phosphorylation of Insulin Receptor Substrate-1 (IRS-1), The Journal of Biological Chemistry, (2001), vol. 276, No. 17, pp. 14459-14465.

Malmqvist, Magnus et al., Biomolecular Interaction Analysis: Affinity Biosensor Technologies for Functional Analysis of Proteins, Current Opinion in Chemical Biology, (1997), vol. 1, pp. 378-383.

Mothe, Isabelle et al., Phosphorylation of Insulin Receptor Substrate-1 on Multiple Serine Residues, 612, 632, 662, and 731, Modulates Insulin Action, The Journal of Biological Chemistry, (1996), vol. 271, No. 19, pp. 11222-11227.

Nave, Barbara T. et al., Mammalian target of rapamycin is a direct target for protein kinase B: identification of a convergence point for opposing effects of insulin and amino-acid deficiency on protein translation, Biochemical Journal, (1999), vol. 344, pp. 427-431.

Paz, Keren et al., Phosphorylation of Insulin Receptor Substrate-1 (IRS-1) by Protein Kinase B Positively Regulates IRS-1 Function, The Journal of Biological Chemistry, (1999), vol. 274, No. 40, pp. 28816-28822.

Qiao, Li-ya et al., In Vivo Phosphorylation of Insulin Receptor Substrate 1 at Serine 789 by a Novel Serine Kinase in Insulin-resistant Rodents, The Journal of Biological Chemistry, (2002), vol. 277, No. 29, pp. 26530-26539.

Ravichandran, Lingamanaidu et al., Protein Kinase C-Zeta Phosphorylates Insulin Receptor Substrate-1 and Impairs Its Ability to Activate Phosphatidylinositol 3-Kinase in Response to Insulin, The Journal Of Biological Chemistry, (2001), vol. 276, No. 5, pp. 3543-3549.

Schmitz-Peiffer, Carsten, Protein Kinase C and Lipid-Induced Insulin Resistance in Skeletal Muscle, Ann. N.Y. Acad. Sci., (2002), vol. 967, pp. 146-157.

Scott; Pamela H. et al., Evidence of insulin-stimulated phosphorylation and activation of the mammalian target of rapamycin mediated by a protein kinase B signaling pathway, Proc. Natl. Acad. Sci. USA, (1998), vol. 95, pp. 7772-7777.

Shepherd, Peter R. et al., Phosphoinositide 3-kinase: the key switch mechanism in insulin signalling, Biochemistry Journal, (1998), vol. 333, pp. 471-490.

Shulman, Gerald I., Cellular mechanisms of insulin resistance, The Journal of Clinical Investigation, (2000), vol. 106, No. 2, pp. 171-176.

Skolnik, E.Y. et al., The SH2/SH3 domain-containing protein GRB2 interacts with tyrosine-phosphorylated IRS1 and Shc: implications for insulin control of ras signalling, The EMBO Journal, (1993), vol. 12, No. 5, pp. 1929-1938.

Smith, Donald B. et al., Single-step purification of polypeptides expressed in *Escherichia coli* as fusions with glutathione S-transferase, Gene, (1988), vol. 67, pp. 31-40.

Standaert, Mary L. et al., Skeletal Muscle Insulin Resistance in Obesity-Associated Type 2 Diabetes in Monkeys Is Linked to a Defect in Insulin Activation of Protein Kinase C, Diabetes, (2002), vol. 51, pp. 2936-2943.

Summers, Scott A. at al., The Role of Glycogen Synthase Kinase 3 Beta in Insulin-stimulated Glucose Metabolism, The Journal of Biological Chemistry, (1999), vol. 274, No. 25, pp. 17934-17940.

Sun, Xiao Jian et al., Pleiotropic Insulin Signals Are Engaged by Multisite Phosphorylation of IRS-1, Molecular and Cellular Biology, (1993), vol. 13, No. 12, pp. 7418-7428.

Sun, Xiao Jian et al., Structure of the insulin receptor substrate IRS-1 defines a unique signal transduction protein , Nature, (1991), vol. 352, pp. 73.

Tanasijevic, Milenko J. et al., Phosphorylation of the Insulin Receptor Substrate IRS-1 by Casein Kinase II, The Journal of Biological Chemistry, (1993), vol. 268, No. 24, pp. 18157-18166.

Tanti, Jean-Francois et al., Serine/Threonine Phosphorylation of Insulin Receptor Substrate 1 Modulates Insulin Receptor Signaling, The Journal of Biological Chemistry, (1994), vol. 269, No. 8, pp. 6051-6057.

Thirone, Ana C. P. et al., Growth Hormone Stimulates the Tyrosine Kinase Activity of JAK2 and Induces Tyrosine Phosphorylation of Insulin Receptor Substrates and Shc in Rat Tissues, Endocrinology, (1999), vol. 140, No. 1, pp. 55-62.

Virkamaki, Antti et al., Protein-protein Interaction in insulin signaling and the molecular mechanisms of insulin resistance, The Journal of Clinical Investigation, (1999), vol. 103, No. 7, pp. 931-943.

White, Morris F., IRS proteins and the common path to diabetes, Am. J. Physiol. Endocrinol. Metab., (2002), vol. 283, pp. E413-E422.

White, Morris F., The IRS-signalling system: A network of docking proteins that mediate insulin action, Molecular and Cellular Biochemistry, (1998), vol. 182, pp. 3-11.

Zick, Yehiel, Insulin resistance: a phosphorylation-based uncoupling of insulin signaling, Trends in Cell Biology, (2001), vol. 11, No. 11, pp. 437-441.

May et al., Effects of protein tyrosine kinase inhibitors on cytokine-induced adhesion molecule expression by human umbilical vein endothelial cells, Br. J. of Pharmacology, vol. 118, 1996, pp. 1761-1771.

Sun et al., Inhibition of protein kinases A and G by hydralazine but not KRN2391 in vitro, Acta Pharmacologica Sinica, vol. 16, No. 3, May 1995, pp. 276-280.

Wang et al., Common elements in interleukin 4 and insulin signaling pathways in factor-dependent hematopoietic cells, PNAS, vol. 90, May 1993, pp. 4032-4036.

Beck et al., Identification of an In Vitro Insulin Receptor Substrate-1 Phosphorylation Site by Negative-ion uLC/ES-AIP-CID-MS Hybrid Scan Technique, J. of Am. Soc. for Mass Spectrometry, vol. 14, No. 4, Apr. 2003, pp. 401-405.

Lehmann et al., Protein kinase C-s phosphorylates serine/threonine residue at the C-terminal binding motif of the tyrosine phosphatase SHP-2 of insulin receptor substrate 1, Signal Transduction, vol. 2, No. 1/2, 2002, pp. 40-45.

Qiao et al., Identification of Enhanced Serine Kinase Activity in Insulin Resistance, J. of Biol. Chem, vol. 274, No. 15, Apr. 9, 1999, pp. 10625-10532.

Sommerfeld et al., In Vitro Phosphorylation of Insulin Receptor Substrate 1 by Protein Kinase C-s Functional Analysis and Identification of Novel Phosphorylation Sites, Biochemistry, vol. 43, 2004, pp. 5888-5901.

Accession No. AA016354 Protein Sequence, Accessed Jan. 30, 2008.

Accession No. AA016354 IRSAL-related protein, nucleotide sequence, Accessed Nov. 24, 2003.

* cited by examiner

A

B

C

A

B

A

B

C

D

E

F

A

B

METHOD FOR IDENTIFYING IRS INHIBITORS OR AGONISTS

BACKGROUND OF THE INVENTION

The present invention relates to a method for the identification of IRS protein kinase inhibitors or agonists; to selected IRS peptides comprising phosphorylation sites for PKC-ζ and other IRS serine kinases; and to the use of these peptides for the identification of a pharmaceutical composition for the treatment of diabetes type 2.

Non-insulin dependent diabetes mellitus (NIDDM) occurs predominantly in adults and is characterized by a reduced sensitivity of tissues being capable of clearing glucose from the blood. In contrast to insulin dependent diabetes mellitus (IDDM, diabetes type I) diabetes type II is not characterized by an impaired insulin secretion from the pancreatic beta cells.

The molecular mechanism leading to decreased insulin sensitivity or even insulin resistance are not yet known, despite of intensive efforts carried out by researchers both in Universities as well as in pharmaceutical industry. Recent studies have elucidated that in diabetes type II the second messenger pathways connecting the activated insulin receptor with GLUT4 translocation and glucose transport are disturbed. Specifically, insulin receptor substrate (IRS)[1] proteins are phosphorylated on multiple tyrosine residues by the activated insulin receptor, the insulin-like-growth factor receptor and JAK1/2 and play a pivotal role in the process of downstream insulin signaling (1, 2, 3). The phosphotyrosine motifs, specifically within IRS-1 and IRS-2, serve as docking sites for a series of adaptor proteins that possess Src homology 2 (SH2) domains including Grb2, the intracellular PTPase SHP-2, Nck, Crk, and phosphatidylinositol-3 kinase (PI-3 kinase) (4-6). PI-3 kinase is composed of a catalytic 110-kDa subunit (p110) and a regulatory 85-kDa subunit (p85) containing two SH2 domains that bind to tyrosine-phosphorylated pYMXM and pYXXM motifs in IRS proteins and induce PI-3 kinase activation (7). This leads to stimulation of additional downstream kinases including the serine/threonine kinase PKB/Akt (8, 9) and the atypical protein kinase C isoforms-ζ and -λ (PKC-ζ/λ) (10, 11) by phosphoinositide-dependent kinase 1. Activation of PKB and PKC-ζ/λ and its downstream signals have been shown to play a critical role in mediating the metabolic actions of insulin such as GLUT4 translocation and glucose transport (10, 11), GSK3 serine phosphorylation and glycogen synthesis (12), PDE serine phosphorylation and anti-lipolysis (13, 14), and mTOR activation and protein synthesis (15, 16).

Dysregulation of the insulin-signaling system is a multifactorial process leading to insulin resistance and type 2 diabetes with the IRS proteins potentially representing a major target (17). Thus, serine/threonine phosphorylation of IRS proteins has been proposed to play a key role both in feedback inhibition of the insulin signal and the development of cellular insulin resistance (for review, see 17-19). Covalent modification of IRS-1 on serine/threonine was shown to impair its insulin-induced tyrosine phosphorylation, the activation of PI 3-kinase and the stimulation of glucose transport (20). In the unstimulated state serine/threonine phosphorylation of IRS-1 occurs constitutively in the cell (21) and it is further promoted by cytokines and metabolites that inhibit signal transduction like tumor necrosis factor (TNF)α (22), free fatty acids, glucose or ceramide (23). Furthermore, hyperphosphorylation of IRS-1 on serine/threonine residues is a common finding during insulin resistance and type 2 diabetes (24).

Despite a key role for the development of insulin resistance, the serine phosphorylation of IRS-1 has remained incompletely understood, mainly because IRS-1 contains more than 100 potential serine phosphorylation sites and because it was shown to represent a substrate for many protein kinases including c-Jun N-terminal kinase (JNK) (25), IkappaB kinase-β (26), MAP kinase (27), Casein kinase (28), glycogensynthase kinase (29), phosphoinositol-3-kinase (30), protein kinase A (31), protein kinase C (32), protein kinase B (PKB) (33) and AMP-activated protein kinase (AMPK) (34). Interestingly, both PKB and AMPK were found to operate as a positive regulator of IRS-1 function supporting the notion that serine/threonine phosphorylation of IRS-1 has a dual role, either to enhance or to terminate insulin signaling (35). Identification of residues within different domains of IRS-1 undergoing serine phosphorylation in response to different stimuli has improved our understanding of this highly complex regulatory step in insulin action. Thus, $Ser^{307}$ which is located near the phosphotyrosine-binding (PTB) domain has been identified as a target for stress-activated kinases including JNK (25) and may also play a role as a negative feedback regulator of insulin action (36). $Ser^{739}$ is targeted by AMPK and positively modulates insulin action (34), however, $Ser^{789}$ phosphorylation by unidentified kinases was also found to attenuate insulin signaling (37). $Ser^{612}$, $Ser^{632}$, $Ser^{662}$ and $Ser^{731}$ are located within or near the PI 3-kinase interaction domain, however, the functional implications of these sites has remained elusive (38-40).

In contrast to the protein kinases mentioned above, protein kinase C (PKC)-ζ, which is an atypical member of the PKC family of serine/threonine kinases, appears to participate both in the downstream transduction of the insulin signal and in the negative feedback control of IRS-1 function (11, 41-44). Thus, PKC-ζ was found to colocalize with GLUT4 and to be essential for insulin-regulated GLUT4 translocation and glucose transport in skeletal muscle (41) and adipocytes (11). Further, defective activation of PKC-ζ may contribute to obesity-dependent development of skeletal muscle insulin resistance (42). Recent data by Quon and co-workers (43) have shown that IRS-1 represents a novel substrate for PKC-ζ and in a parallel study Zick and co-workers (44) found that this process inhibits PI 3-kinase activation, suggesting that PKC-ζ represents a key element in the negative feedback control of insulin action.

In summary, although it is known in the art that IRS, especially IRS-1 interacts with PKC-ζ, the nature of this interaction is not known. Consequently, there are no agents known in the art interacting with IRS-PKC-ζ interaction. However, such agents would be highly needed since it is very likely that an inhibition of the interaction of IRS and PKC-ζ would result in down-regulation of the inhibition of IRS and, more downstream, PI 3-kinase which in turn would result in an improvement in GLUT4 translokation and glucose transport.

Upper panel: The relative positions of the pleckstrin homology (PH) and phosphotyrosine-binding (PTB) domain are indicated followed by a C-terminal tail that contains numerous tyrosine phosphorylation sites. Potential binding partners including PI 3-kinase, Grb2 and SHP-2 are also shown. Middle panel: Known (S307, 612, 632, 789) and potential serine phosphorylation sites are highlighted. Bottom panel: Construction of a GST-fusion protein containing aa 449-664 of rat IRS-1 including the major binding site of the PI 3-kinase.

Figure 2:
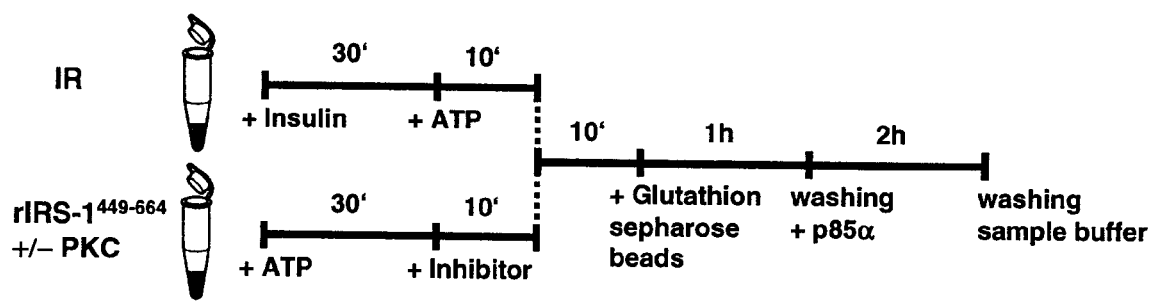
Figure 2:
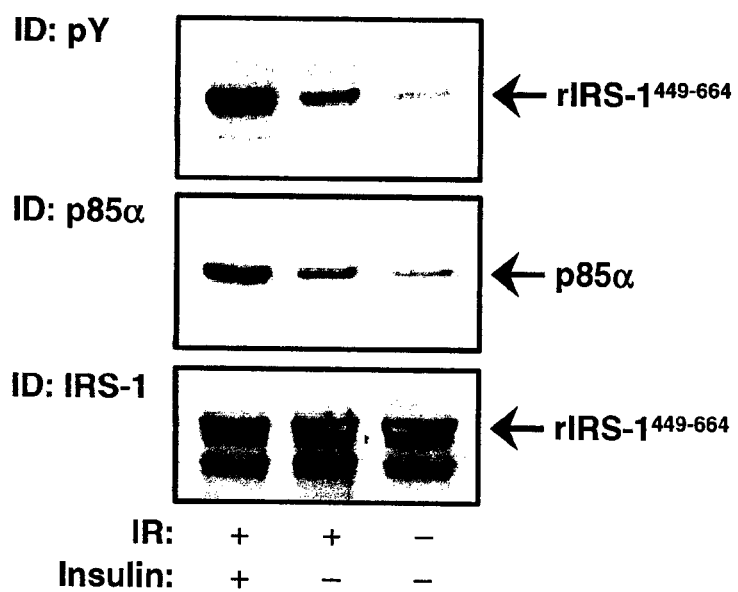
Figure 2:
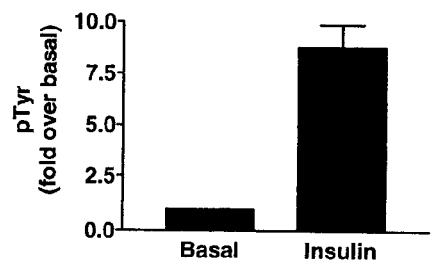

FIG. 2: Tyrosine phosphorylation of rIRS-1$^{449-664}$ and interaction with p85α subunit of PI 3-kinase.

(A) Schematic diagram of the experimental procedure. 5 μg IR was autophosphorylated for 10 min at 30° C. in phosphorylation buffer after a 30 min preincubation with 100 nM insulin. Substrate phosphorylation was subsequently initiated by addition of autophosphorylated IR to aliquots of 1 μg rIRS-1$^{449-664}$. The reaction proceeded for 10 min and then glutathione sepharose beads were added and samples were incubated at 4° C. on a rotator for 1 h. Pellets were washed three times with binding buffer, 0.5 pg recombinant p85α was added and incubation was continued for 2 h. After washing, bound proteins were eluted by addition of 2× sample buffer followed by boiling for 5 min. (B) Eluted proteins were resolved by SDS-PAGE and were analyzed by immunoblotting using antibodies against phosphotyrosine, p85α and IRS-1, as detailed in the Methods section. Representative blots out of six separate experiments are shown. (C) Quantification of rIRS-1$^{449-664}$ tyrosine phosphorylation was obtained using Lumi Imager software. Data are mean values±SEM (n=10).

Figure 3:
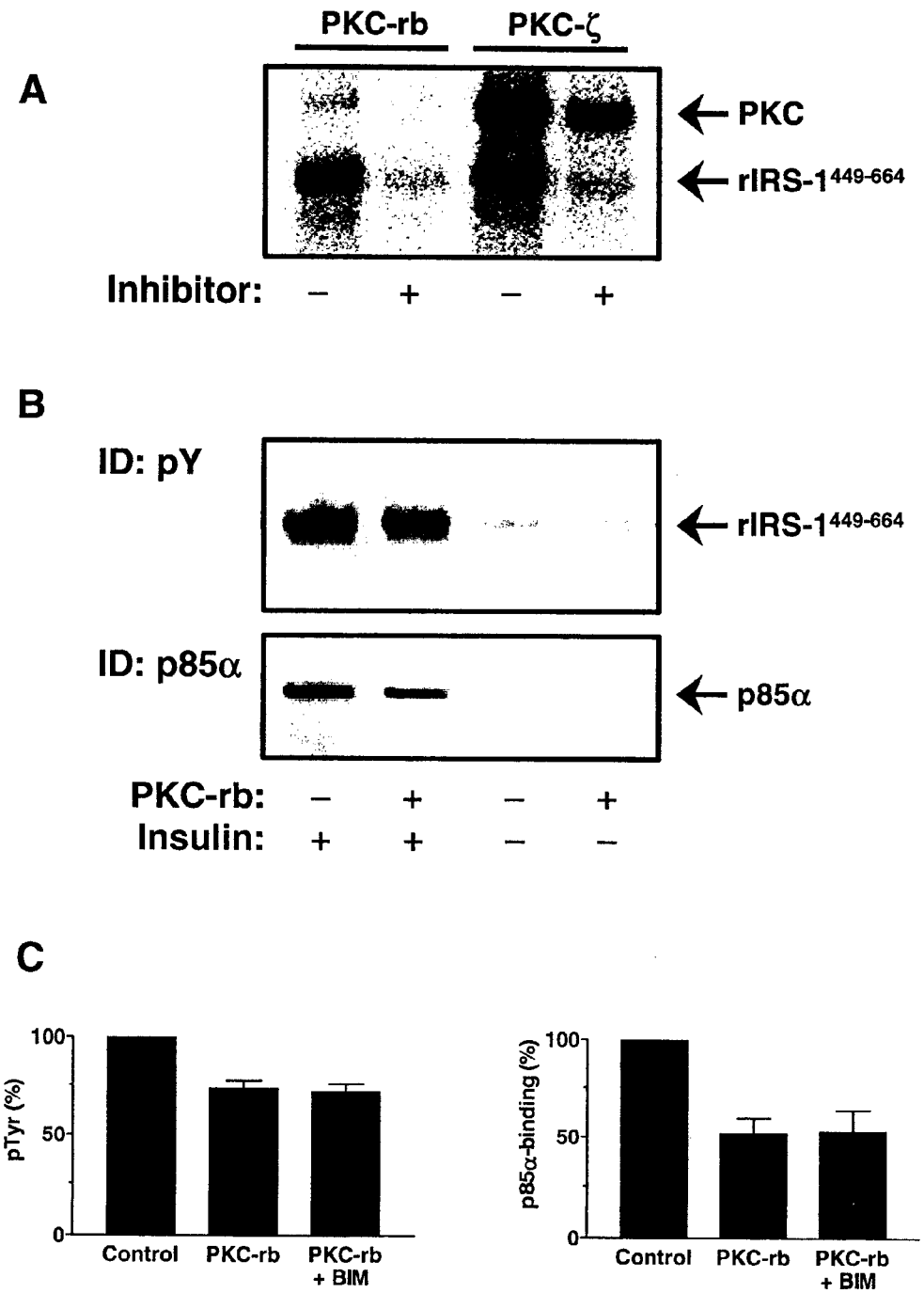

FIG. 3: Effect of PKC from rat brain on tyrosine phosphorylation of rIRS-1$^{449-664}$ and interaction with p85α.

(A) 1 μg of rIRS-1$^{449-664}$ was incubated with 0.5 μg PKC from rat brain (PKC-rb) or 0.5 μg PKC-ζ in the presence of 2 μCi ($^{32}$P)-ATP (final conc. 50 μM), as detailed in Methods. The reaction was inhibited by bisindolylmaleimide I (BIM) or pseudosubstrate peptide for PKC-rb or PKC-ζ, respectively. Proteins were resolved by SDS-PAGE and subjected to autoradiography. (B) Tyrosine phosphorylation of rIRS-1$^{449-664}$ by IR and interaction with p85α was determined as described in FIG. 2. rIRS-1$^{449-664}$ was preincubated with 0.5 μg PKC-rb for 30 min. Representative blots are shown. (C) Quantification of the inhibitory effect of PKC-rb on insulin stimulated tyrosine phosphorylation and p85α interaction with the insulin-stimulated value set as 100%. When present, BIM was added for 10 min before starting substrate phosphorylation by IR (see FIG. 2). Data are mean values±SEM (n=6-9).

Figure 4:
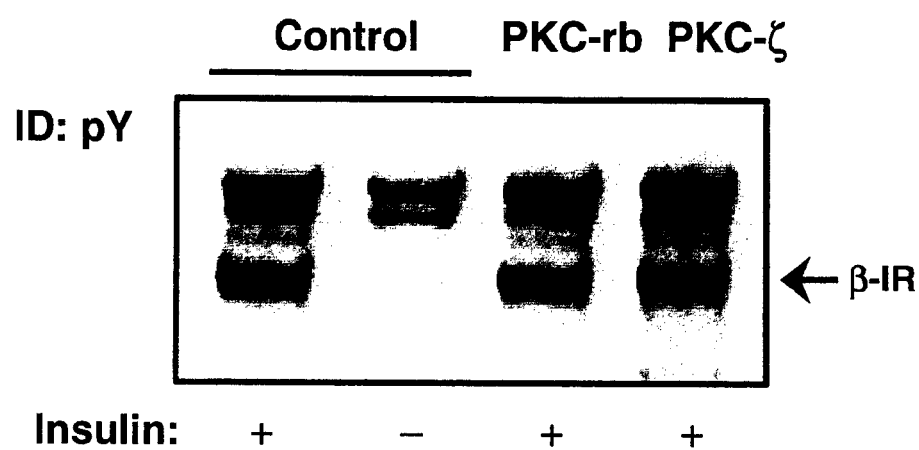
Figure 4:
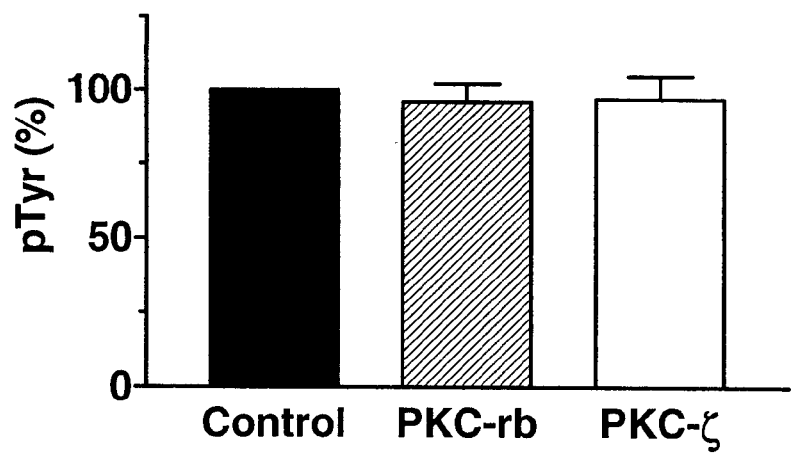

FIG. 4: Effect of PKC isoforms on IR autophosphorylation.

(A) Autophosphorylation of IR was conducted as outlined in FIG. 2. Either PKC-rb or PKC-ζ was added after 10 min of autophosphorylation and incubation was continued for another 10 min. Tyrosine phosphorylation of IR β-subunit was then analyzed by immunoblotting. (B) Quantification of blots was obtained using Lumi Imager software. Data are mean values±SEM (n=4-6).

Figure 5:
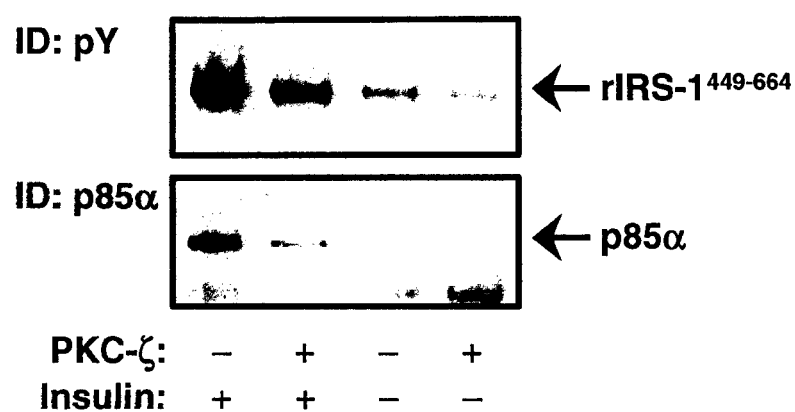
Figure 5:
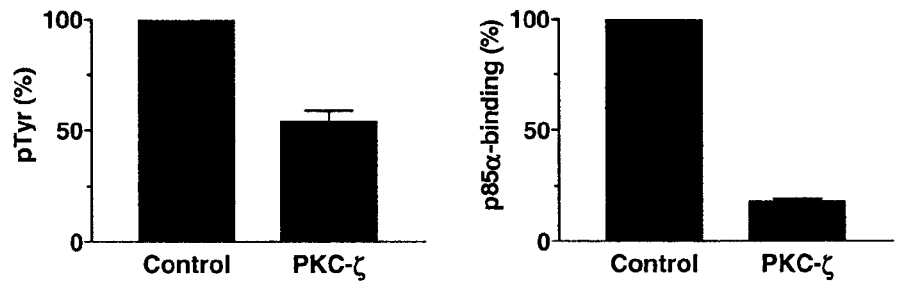

FIG. 5: Effect of PKC-ζ on tyrosine phosphorylation of rIRS-1$^{449-664}$ and interaction with p85α.

(A) rIRS-1$^{449-664}$ was preincubated with PKC-ζ (0.5 μg) for 30 min. Tyrosine phosphorylation by IR and interaction with p85α was determined by immunoblotting, as detailed in FIG. 2.(B) Quantification of the inhibitory effect of PKC-ζ was performed as described in FIG. 3. Data are mean values±SEM (n=3).

Figure 6:
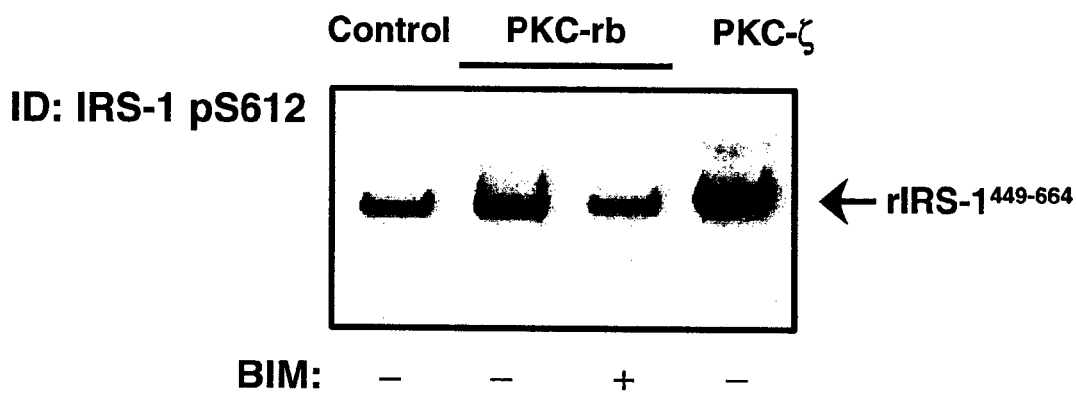
Figure 6:
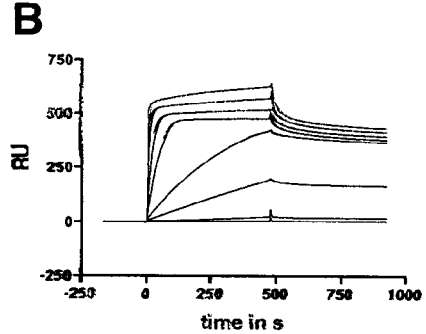
Figure 6:
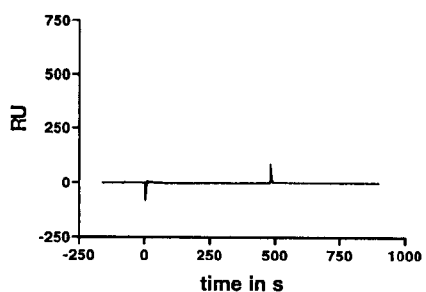
Figure 6:
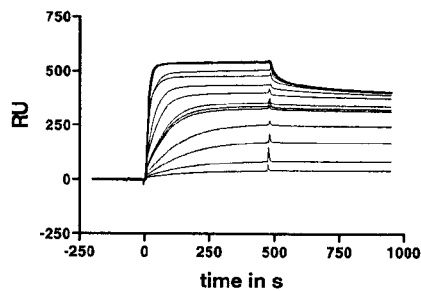
Figure 6:
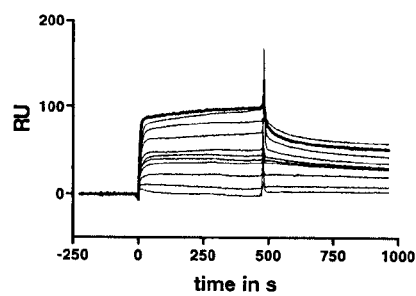
Figure 6:
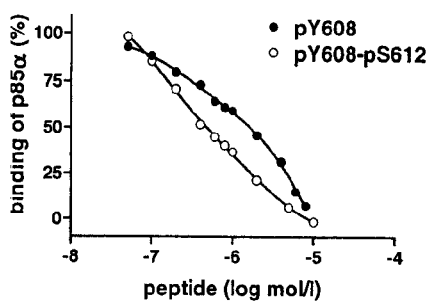

FIG. 6: Identification of IRS-1 serine 612 as a target of PKC and interaction analysis with p85α using surface plasmon resonance.

(A) 0.5 μg of rIRS-1$^{449-664}$ was incubated with 0.5 μg of the different PKCs for 30 min at 30° C. and immunoblotted with an antibody against phosphoserine 612. A representative experiment is shown. (B) Binding of p85α to immobilized peptides corresponding to the IRS-1 amino acids 605 to 615 with phosphotyrosine 608 or (C) without phosphotyrosine using surface plasmon resonance (pY608 -DDGpYMPM-SPGV and Y608 -DDGYMPMSPGV). Protein concentrations of p85α used were (from bottom to top): 1, 5,10, 25, 50,100, 250, 500 nM. (D) Inhibition of p85α binding by competition with soluble peptides pY608-DDGpYMPM-SPGV or (E) pY608-pS612-DDGpYMPMpSPGV. The soluble peptides were also immobilized on the chip. (F) Half-maximum inhibitory concentrations (IC50) were obtained by plotting the SPR response at equilibrium (440 s after injection) versus the log peptide concentration. IC50 for pY608: 0.26 μmol/l, 16.56 μmol/l and for pY608-pS612: 0.15 μmol/l, 2.88 μmol/l.

Figure 7:
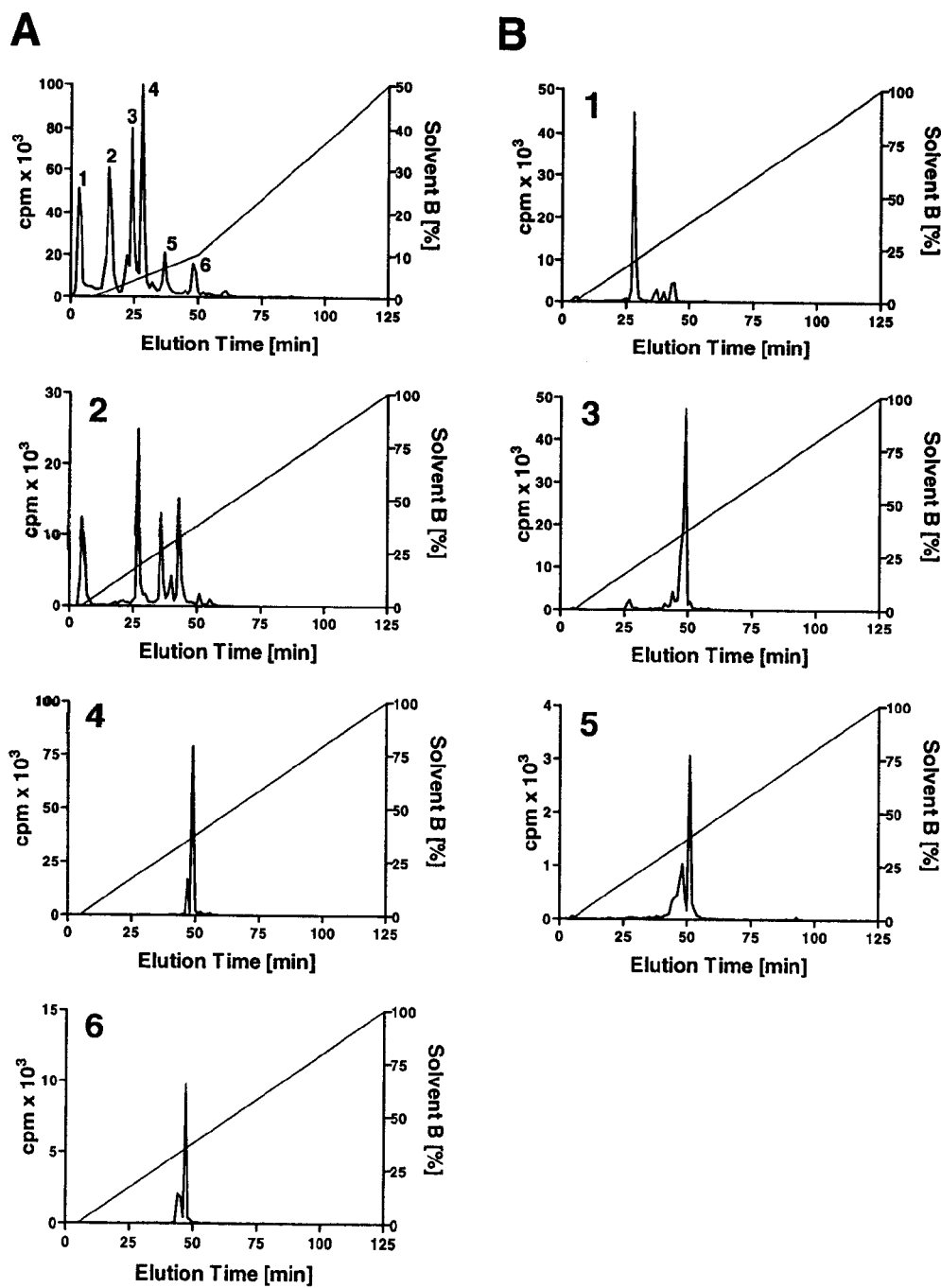

FIG. 7: HPLC analysis of tryptic phosphopeptides derived from rIRS-1$^{449-664}$ phosphorylated by PKC-ζ.

Five nanomoles of rIRS-1$^{449-664}$ were phosphorylated for 60 min using 0.5 nmol of PKC-ζ. Proteins were separated by SDS-PAGE and the excised rIRS-1$^{449-664}$ was digested with trypsin. The recovered $^{32}$P-radiolabeled peptide mixture was separated by ion exchange (A) and C18 reversed phase HPLC (B). The radioactivity of the collected fractions was determined by Cerenkov counting. After reversed phase HPLC radioactive fractions were analyzed by mass spectrometry.

Figure 8:
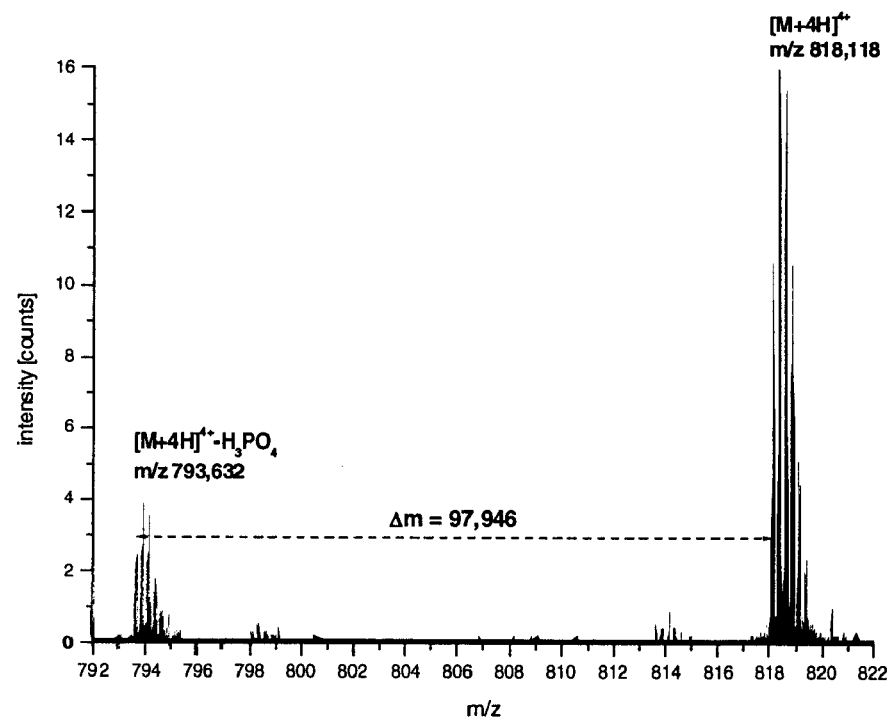
Figure 8:
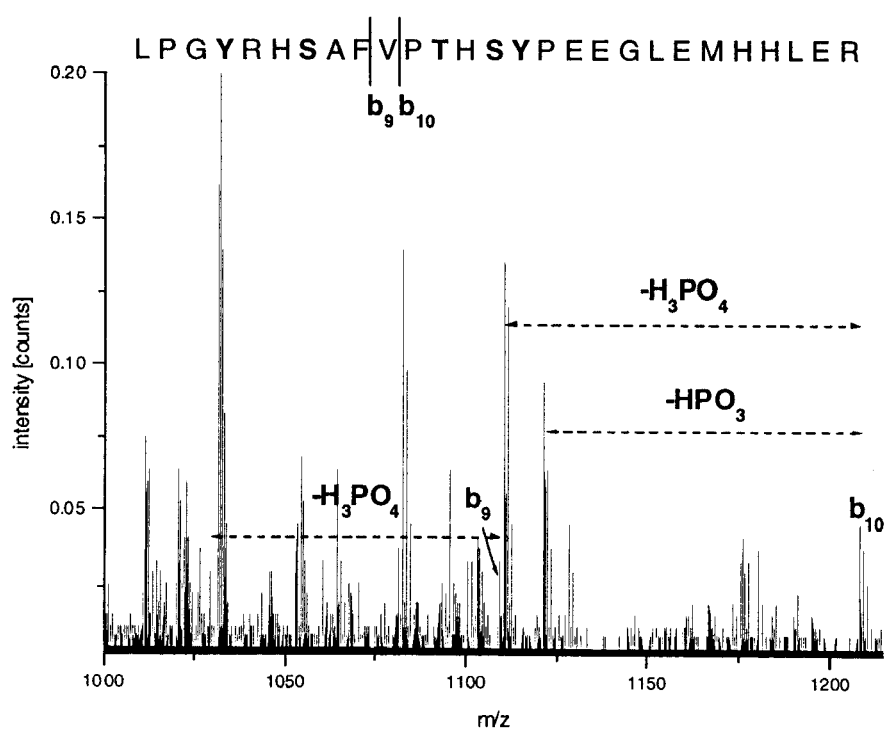

FIG. 8: ESI-MS/MS spectra from the phosphopeptid 352-378.

(A) Loss of phosphoric acid from the parent ion [M+4H]$^{4+}$=818.11, indicating the phosphorylation. (B) Dephosphorylation of the fragment ion $b_9$ and $b_{10}$, indicating the phosphorylation site.

Figure 9:
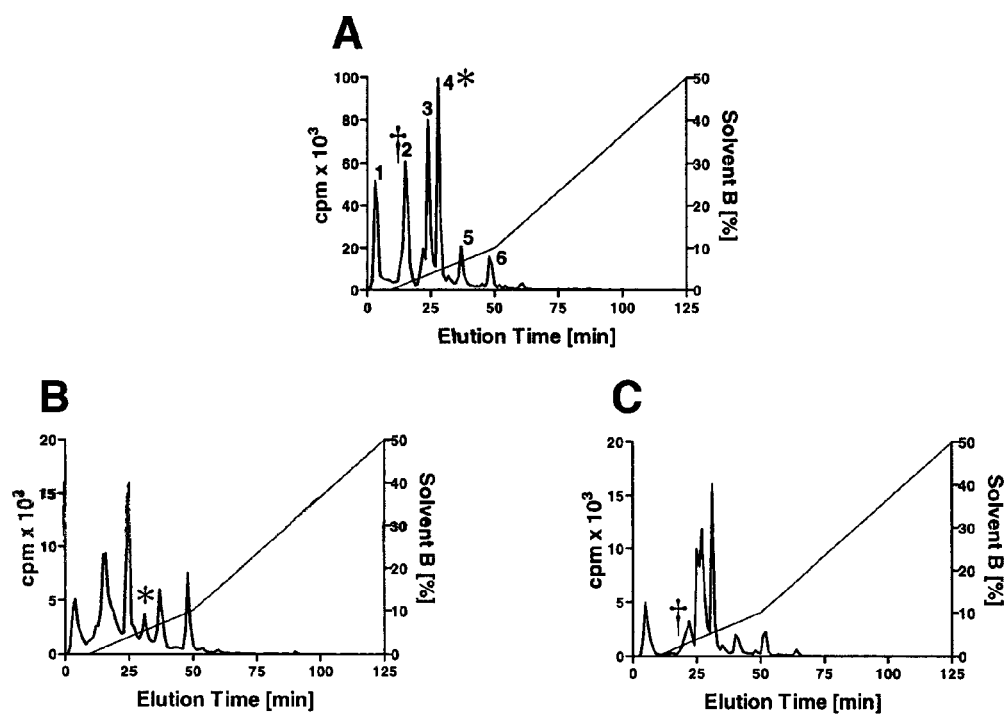

FIG. 9: HPLC analysis of tryptic phosphopeptides of rIRS-1$^{449-664}$ and mutants S570A and S612A.

HPLC analysis of tryptic peptides generated from wildtype rIRS-1$^{449-664}$ (A,) rIRS-1$^{449-664}$ S570A (B), and rIRS-1$^{449-664}$ S612A (C) phosphorylated with recombinant PKC-ζ is shown. Representative HPLC profiles are presented.

Figure 10:
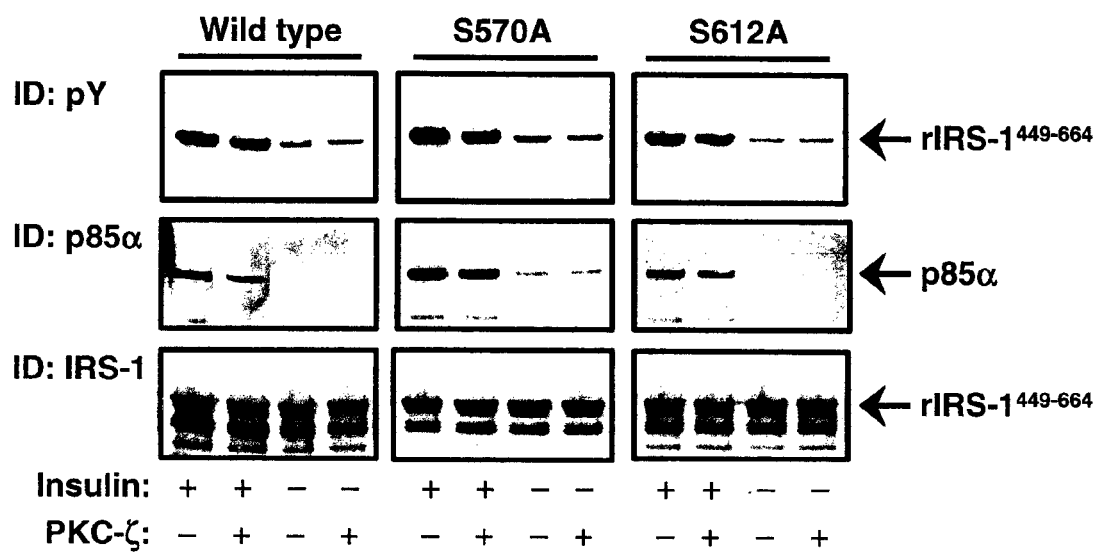
Figure 10:
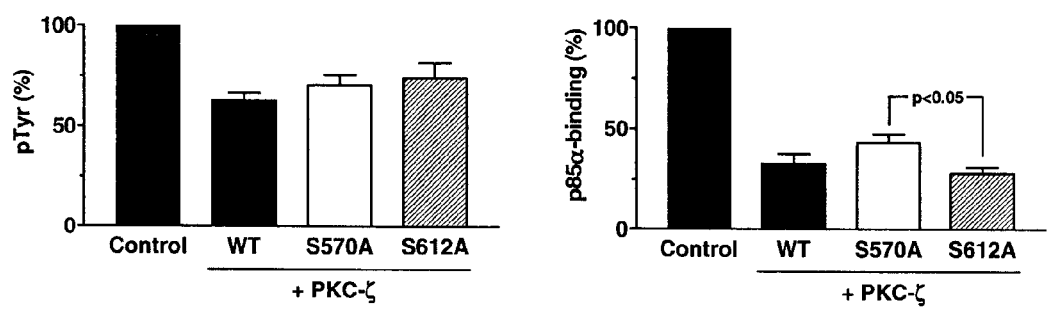

FIG. 10: Functional analysis of serine 570 and serine 612.

(A) rIRS-1$^{449-664}$ and the indicated mutants were preincubated with PKC-ζ and subjected to tyrosine phosphorylation by IR and interaction with p85α, as outlined in FIG. 5. Representative Western blots are shown. (B) Blots were quantified using Lumi Imager software and data are expressed relative to the insulin-stimulated control value set as 100%. Results are mean values±SEM (n=3).

DETAILED DESCRIPTION OF THE INVENTION

Disclosed herein is a method for the identification of an IRS protein kinase inhibitor, the method comprising the steps of
a) bringing into contact PKC-ζ with at least one IRS peptide comprising at least one PKC-ζ-Ser-phosphorylation site in the presence of at least one possible inhibitor, and
b) measuring the phosphorylation of the PKC-ζ-Ser-phosphorylation site.

The present invention is based on the surprising identification of specific serine phosphorylation sites in the sequence of IRS, which are specifically recognized by PKC-ζ. Consequently, in the context of the present invention, the molecular mechanism providing the IRS-PKC-ζ interaction were identified. Moreover its likely that other protein kinases like c-Jun N-terminal kinase (JNK), IkappaB kinase-β, MAP kinase, Casein kinase, glycogensynthase kinase, phosphoinositol-3-kinase, protein kinase A, protein kinase C, protein kinase B 8PKB) and AMP-activated protein kinase (AMPK) might be able to recognize these phosphorylation sites. Therefore the determination of the serine sites, which are phosphorylated by protein kinases, especially PKC-ζ, enables the identification of molecules interfering with this interaction, either in an antagonistic or agonistic way.

In the context of the present invention, the term "IRS protein kinase inhibitor" relates to a substance which interferes with the interaction between IRS and a protein kinase, exemplified by PKC-ζ.

In the context of the present invention, the term "IRS peptide" relates to a peptide comprising a stretch of at least 5, preferably 7, preferably at least 10 amino acids of IRS. The term "IRS peptide" includes that the IRS-peptide may comprise, in addition to the stretch of amino acids derived from IRS, further amino acids which are not IRS derived.

All methods of the invention are preferably carried out in vitro.

PKC-ζ is commercially available, e.g. from CalBiochem (San Diego, Calif., USA). Furthermore, methods for the isolation of PKC-ζ are described in the literature cited in the present application.

The sequence of IRS, especially IRS-1 and IRS-2 from different species are known in the art. The rat IRS-1 sequence is herein provided as SEQ ID NO: 16.

Methods for the production of proteins and consequently of IRS are known in the art and enclude e.g. the expression of the protein in appropriate cells starting from a cDNA or the production by subsequent addition of amino acids to a starting amino acid (see Current Protocols, John Wiley & Sons, Inc., New York)

Furthermore, methods for the production of protein fragments are known in the art (see above) and include the cleavage of the protein with appropriate proteases or the generation of nucleic acid fragments encoding the protein fragments and subsequent expression of the fragments in appropriate cells.

Methods for the production of mutated proteins, e.g. by exchanging one or more amino acids or by deleting stretches of amino acids, are known in the art (see above). These methods include site directed mutagenesis of the IRS gene and expressing the modified gene in appropriate cells.

According to a preferred embodiment, a reduced phosphorylation of the PKC-ζ-Ser-phosphorylation site in comparison to the phosphorylation in the absence of the at least one possible inhibitor is indicative for the inhibitory properties of the possible inhibitor.

Preferably, PKC-ζ is of mammalian, preferably, of rodent or human origin, more preferably of rat or human origin.

According to a preferred embodiment of the present invention, the IRS peptide is derived from an IRS, preferably IRS-1, of mammalian, preferably of human or rodent, more preferably of rat origin.

Preferably, the IRS-1 is of rat origin and the at least one PKC-ζ-Ser-phosphorylation site is selected from the group consisting of Ser 458, 469, 481, 498, 522, 526, 530, 536, 538, 539, 542, 560, 570, 577, 599, 600, 612, 620, 632, 635, 662, and 664 wherein the sequence numbers correspond to rat IRS-1 as depicted in SEQ ID NO:16. Furthermore, the IRS-1 may be of human origin and the at least one PKC-ζ-Ser-phosphorylation site is selected from Ser-residues corresponding to the above Ser-residues of the rat IRS-1.

Preferably, the PKC-ζ-Ser-phosphorylation site in the context of the present invention may be selected from the group consisting of $Ser^{498}$, $Ser^{570}$ and $Ser^{612}$, more preferably $Ser^{570}$.

According to a most preferred embodiment of the present invention, the peptide is $rIRS^{449-664}$ (SEQ ID NO: 17).

Preferably, the inhibitor is selected from the group consisting of binding peptides, antibodies, and Low molecular weight compounds (LMWs).

The term "binding protein" or "binding peptide" refers to a class of proteins or peptides which bind and inhibit IRS including, without limitation, polyclonal or monoclonal antibodies, antibody fragments and protein scaffolds directed against IRS, e.g. anticalins which are directed against IRS The procedure for preparing an antibody or antibody fragment is effected in accordance with methods which are well known to the skilled person, e.g. by immunizing a mammal, for example a rabbit, with IRS, where appropriate in the presence of, for example, Freund's adjuvant and/or aluminum hydroxide gels (see, for example, Diamond, B. A. et al. (1981) The New England Journal of Medicine: 1344-1349). The polyclonal antibodies which are formed in the animal as a result of an immunological reaction can subsequently be isolated from the blood using well known methods and, for example, purified by means of column chromatography. Monoclonal antibodies can, for example, be prepared in accordance with the known method of Winter & Milstein (Winter, G. & Milstein, C. (1991) Nature, 349, 293-299).

According to the present invention the term antibody or antibody fragment is also understood as meaning antibodies or antigen-binding parts thereof which have been prepared recombinantly and, where appropriate, modified, such as chimeric antibodies, humanized antibodies, multifunctional antibodies, bispecific or oligospecific antibodies, single-stranded antibodies and F(ab) or F(ab)2 fragments (see, for example, EP B1 0 368 684, U.S. Pat. No. 4,816,567, U.S. Pat. No. 4,816,397, WO 88/01649, WO 93/06213 or WO 98/24884, all of which arc incorporated by reference herein).

As an alternative to the classical antibodies it is also possible, for example, to use protein scaffolds against IRS, e.g. anticalins which are based on lipocalin (Beste et al. (1999) Proc. Natl. Acad. Sci. USA, 96,1898-1903). The natural ligand-binding sites of the lipocalins, for example the retinol-binding protein or the bilin-binding protein, can be altered, for example by means of a "combinatorial protein design" approach, in such a way that they bind to selected haptens, here to IRS (Skerra, 2000, Biochim. Biophys. Acta, 1482, 337-50). Other known protein scaffolds are known as being alternatives to antibodies for molecular recognition (Skerra (2000) J. Mol. Recognit., 13, 167-187).

LMWs are molecules which are not proteins, peptides antibodies or nucleic acids, and which exhibit a molecular weight of less than 5000 Da, preferably less than 2000 Da, more preferably less than 500 Da. Such LMWs may be identified in High-Through-Put procedures starting from libraries.

The inhibitor can be in the form of a natural product extract, either in crude or in purified form. The extract can be produced according to standard procedures, such as water and/or alcohol and/or organic solvent extraction and/or column chromatography and/or precipitation from an animal, plant or microbial source, such as snake poison, leaves or microbial fermentation broths.

In the context of the present invention, IRS and PKC-ζ are provided e.g. in an assay system and brought directly or indirectly into contact with a test compound, in particular a biochemical or chemical test compound, e.g. in the form of a chemical compound library. Then, the influence of the test compound on the phosphorylation of IRS is measured or detected. Thereafter, suitable inhibitors can be analyzed and/or isolated. For the screening of chemical compound libraries, the use of high-throughput assays are preferred which are known to the skilled person or which are commercially available.

According to the present invention the term "chemical compound library" refers to a plurality of chemical compounds that have been assembled from any of multiple sources, including chemically synthesized molecules and natural products, or that have been generated by combinatorial chemistry techniques.

In general, the influence of the test compound on the interaction is measured or detected by determining the degree of phosphorylation of the IRS peptide. This can be done by using phosphor-specific antibodies. Such antibodies are known in the art and available e.g. from Clonetech, Santa Cruz and Cellsignal.

Alternatively, the degree of phosphorylation may be measured by using radio labeled ATP in the assay. The ATP can be labeled with 32-P or 33-P, and the amount of radioactive phosphate incorporated into the IRS can be measured by methods known in the art (see Example 2, 9.). For example, the intensity of a signal measured by auto radiography may be indicative for the degree of phosphorylation.

Advantageously the method of the present invention is carried out in a robotics system e.g. including robotic plating and a robotic liquid transfer system, e.g. using micro fluidics, i.e. channeled structured.

In another embodiment of the present invention, the method is carried out in form of a high-through put screening system. In such a system advantageously the screening method is automated and miniaturized, in particular it uses miniaturized wells and micro fluidics controlled by a roboter.

The invention further relates to a method for the identification of an IRS agonist, comprising the steps of
a) bringing into contact PKC-ζ with at least one IRS peptide comprising at least one PKC-ζ-Ser-phosphorylation site in the presence of at least one possible agonist comprising at least one PKC-ζ-Ser-phosphorylation site, and
b) measuring the phosphorylation of the PKC-ζ-Ser-phosphorylation site of the possible agonist.

For this method of the invention, with respect to PKC-ζ and IRS, the same embodiments as for the above disclosed method apply.

In preferred embodiment, the agonist is a peptide. Peptide libraries which could be used in the context of the present invention are known in the art.

According to a preferred embodiment of this method of the invention, an increased phosphorylation of the PKC-ζ-Ser-phosphorylation site of the agonist in comparison to the phosphorylation of the PKC-ζ-Ser-phosphorylation site of the IRS peptide is indicative for the agonistic properties of the possible agonist.

The invention further relates to a method for the determination of PKC-ζ activity, comprising the steps of
a) bringing into contact PKC-ζ with at least one IRS peptide comprising at least one PKC-ζ-Ser-phosphorylation site in the presence of at least one possible inhibitor, and
b) measuring the phosphorylation of the PKC-ζ-Ser-phosphorylation site.

Consequently, the present invention provides a method to measure the activity of PKC-ζ. Such a method is especially useful when the activity of PKC-ζ from different patients has to measured in order to gain more information about the signal transduction system in patients, especially diabetic patients.

Within this method of the invention, PKC-ζ is preferably of mammalian, more preferably of human origin.

With respect to this method of the invention and to the IRS used therein, the same applies as for the other method of the invention as disclosed above.

The invention further relates to an IRS-1 peptide comprising $Ser^{570}$, preferably $IRS-1^{449-664}$ as shown in SEQ ID NO: 17 or to its human homologue.

Within the present invention, it has turned out that this peptide of the invention is especially useful for the identification of IRS analogues or inhibitors.

The invention further provides a kit comprising
a) at least one IRS peptide,
b) a PKC-ζ preparation, and
c) at least one possible IRS protein kinase inhibitor or agonist.

As already discussed above, such a kit is extremely useful for the identification of IRS protein kinase inhibitors. Its individual components have already been discussed above.

In a further aspect, the present invention provides an IRS-1 peptide, wherein $Ser^{570}$ and/or $Ser^{612}$ are mutated, preferably to alanine. Such a peptide is useful for blocking PKC-ζ activity in vitro or in vivo.

The invention further relates to the use of an IRS peptide as defined above for the production of antibodies, preferably against a PKC-ζ-Ser-phosphorylation site, preferably against $Ser^{498}$, $Ser^{570}$ and $Ser^{612}$, more preferably against $Ser^{570}$. Consequently, with the help of the IRS peptides as defined in the present invention, it is possible to produce IRS specific antibodies, especially antibodies which are directed against PKC-ζ phosphorylation sites. Such antibodies can serve both in in vitro diagnostics as well as in pharmaceutical compositions.

In a further aspect, the present invention relates to the use of an IRS peptide as defined above or of an IRS-1 peptide with mutated Ser-sites as defined above for the preparation of a pharmaceutical composition for the treatment of diabetes type 2. Such peptides may inhibit the interaction between IRS and PKC-ζ and may, therefore, serve as antagonists of IRS phosphorylation.

For the production of the pharmaceutical composition the IRS protein kinase inhibitors or agonists as identified in the present invention or the peptides of the present invention are usually formulated with one or more pharmaceutically acceptable additives or auxiliary substances, such as physiological buffer solution, e.g. sodium chloride solution, demineralized water, stabilizers, such as protease or nuclease inhibitors, preferably aprotinin, ε-aminocaproic acid or pepstatin A or sequestering agents such as EDTA, gel formulations, such as white vaseline, low-viscosity paraffin and/or yellow wax, etc. depending on the kind of administration.

Suitable further additives are, for example, detergents, such as, for example, Triton X-100 or sodium deoxycholate, but also polyols, such as, for example, polyethylene glycol or glycerol, sugars, such as, for example, sucrose or glucose, zwitterionic compounds, such as, for example, amino acids such as glycine or in particular taurine or betaine and/or a protein, such as, for example, bovine or human serum albumin. Detergents, polyols and/or zwitterionic compounds are preferred.

The physiological buffer solution preferably has a pH of approx. 6.0-8.0, expecially a pH of approx. 6.8-7.8, in particular a pH of approx. 7.4, and/or an osmolarity of approx. 200-400 milliosmol/liter, preferably of approx. 290-310 milliosmol/liter. The pH of the pharmaceutical composition is in general adjusted using a suitable organic or inorganic buffer, such as, for example, preferably using a phosphate buffer, tris buffer (tris(hydroxymethyl)aminomethane), HEPES buffer ([4-(2-hydroxyethyl)piperazino]ethanesulphonic acid) or MOPS buffer (3-morpholino-1-propanesulphonic acid). The choice of the respective buffer in general depends on the desired buffer molarity. Phosphate buffer is suitable, for example, for injection and infusion solutions.

The pharmaceutical composition can be administered in a conventional manner, e.g. by means of oral dosage forms, such as, for example, tablets or capsules, by means of the mucous membranes, for example the nose or the oral cavity, in the form of depositories implanted under the skin, by means of injections, infusions or gels which contain the pharmaceutical compositions according to the invention. It is further possible to administer the pharmaceutical composition topically and locally, if appropriate, in the form of liposome complexes. Furthermore, the treatment can be carried out by means of a transdermal therapeutic system (TTS), which makes possible a temporally controlled release of the pharmaceutical compositions. TTS are known for example, from EP 0 944 398 A1, EP 0 916 336 A1, EP 0 889 723 A1 or EP 0 852 493 A1, all of which are incorporated by reference herein.

Injection solutions are in general used if only relatively small amounts of a solution or suspension, for example about 1 to about 20 ml, are to be administered to the body. Infusion solutions are in general used if a larger amount of a solution or suspension, for example one or more liters, are to be administered. Since, in contrast to the infusion solution, only a few milliliters are administered in the case of injection solutions, small differences from the pH and from the osmotic pressure of the blood or the tissue fluid in the injection do not make themselves noticeable or only make themselves noticeable to an insignificant extent with respect to pain sensation. Dilution of the formulation according to the invention before use is therefore in general not necessary. In the case of the administration of relatively large amounts, however, the formulation according to the invention should be diluted briefly before administration to such an extent that an at least approximately isotonic solution is obtained. An example of an isotonic solution is a 0.9% strength sodium chloride solution. In the case of infusion, the dilution can be carried out, for example, using sterile water while the administration can be carried out, for example, via a so-called bypass.

The invention further relates to a method for the preparation of a pharmaceutical composition, comprising the steps:
  a) identifying an IRS protein kinase inhibitor or agonist as defined above,
  b) providing adequate amounts of the IRS protein kinase inhibitor, and
  c) formulating the IRS protein kinase inhibitor into a pharmaceutical composition, optionally in combination with a pharmaceutical acceptable carrier.

The invention is further described by the following examples and figures, which are not intended to limit the scope of the present invention.

EXAMPLES

Example 1

Oligonucleotide primers were obtained from MWG-Biotech (Ebersberg, Germany). BL21 Codon Plus and QuikChange™ Site-Directed Mutagenesis Kit were purchased from Stratagene (La Jolla, Calif., USA). One Shot TOP 10 Competent Cells were from Invitrogen (Karlsruhe, Germany). A plasmid miniprep kit was obtained from Qiagen (Hilden, Germany). A polyclonal anti-IRS-1 antiserum was a gift from Dr. J. A. Maassen (Leiden, The Netherlands). Anti-phosphotyrosine antibody (RC20) coupled to horseradish peroxidase and anti-p85α antibody were obtained from Transduction Laboratories, Inc. (Lexington, Ky., USA). Monoclonal anti-IRβ antibody was supplied from Oncogene (Cambridge, Mass., USA). Anti-IRS-1 pS616 antibody was from Biosource (Camarillo, Calif., USA). HRP-conjugated anti-rabbit and anti-mouse IgG antibody as secondary antibody for enhanced chemiluminescence (ECL) detection was from Promega Corp. (Mannheim, Germany). Protein kinase C from rat brain (PKC-rb), recombinant human protein kinase C-ζ, bisindolylmaleimide I (BIM), and PKC-ζ pseudosubstrate inhibitor were obtained from Calbiochem (San Diego, Calif., USA). Alpha Thrombin was purchased from Upstate Biotechnology Inc. (Lake Placid, N.Y., USA). Enzymes for molecular biology, Complete protease inhibitor cocktail, and modified trypsin sequencing grade were obtained from Roche (Mannheim, Germany). Okadaic acid, phosphatidylserine, and wheat germ agglutinin (Triticum vulgaris) were purchased from SIGMA (München, Germany). IRS-1 peptides were synthesized by Dr. Hoffmann (BMFZ, University of Düsseldorf, Düsseldorf, Germany). Chemicals for SDS-PAGE, GST gene fusion vector pGEX-5X-3, Glutathione Sepharose® 4B and [γ-$^{32}$P]ATP were supplied by Amersham Biosciences (Freiburg, Germany). GelCode Blue Stain reagent, Restore™ Western Blot stripping buffer and SuperSignal Substrate was obtained from Pierce (Rockford, USA). Biacore X and sensor chip CM5 are products of Biacore (Freiburg, Germany). All other chemicals were of the highest grade commercially available.

Example 2

Construction and Expression of Fusion Proteins

The regulatory p85α subunit of bovine PI 3-kinase cloned into the expression vector pGEX-2T was a kind gift of Dr. P. Shepherd (London, UK). A glutathione S-transferase (GST) fusion protein containing the amino acids 449-664 of rat IRS-1 (rIRS-1$^{449-664}$, $M_w$ of 51.2 kDa) was prepared based on the method described by Smith and Johnson (40) using the pGEX-5X-3 vector. Corresponding rat cDNA was generated from RNA isolated from rat heart by reverse transcription using avian myeloblastosis virus reverse transcriptase and subsequent amplification by polymerase chain reaction using Pwo DNA Polymerase and the following oligonucleotide primers: 5'-primer, ATATTGTCGACCAC-ACCCCAC-CAGCCAGG, 3'-primer, ATGTACTACTACAGAGGGTC-ACGCCGGCGTAAGAATA (SEQ ID NO: 1 and 2). The PCR products were isolated, digested with appropriate restriction enzymes and subcloned into pGEX-5X-3. Identity of the rat IRS-1 clone was verified by restriction endonuclease analysis and nucleotide sequencing. This vector and the p85α-pGEX-2T construct were used to transform *Escherichia coli* BL21.

Transformed cells were grown to an $A_{600\,nm}$ of 0.6-0.8 in 2× YTA medium (16 g/l tryptone, 10 g/l yeast, NaCl 5 g/l) supplemented with 0.1 mg/ml ampicillin and induced for 2 h with 0.1 mM isopropyl-β-D-thiogalactoside (IPTG). Fusion proteins were purified by affinity chromatography on glutathione-sepharose columns and eluted by 10 mM glutathione in 50 mM Tris-HCl (pH 8.0). The GST part of the p85α GST-fusion protein was proteolytically removed using bovine thrombin in PBS. The protease was added to the fusion protein bound to the glutathione sepharose column, incubated for 2 h at room temperature and then the eluate was collected. Protein was determined using a modification of the Bio-Rad protein assay. All GST fusion proteins had the expected molecular weight when analyzed by sodium dodecyl sulphate (SDS) polyacrylamide gel electrophoresis (PAGE).

Insulin Receptor Kinase Preparation

Rat liver was rapidly removed, immediately frozen in liquid nitrogen and processed as described (41). Briefly, 3.5 vol/wt of an ice-cold buffer consisting of 50 mM Hepes (pH 7.4), 1% Triton X-100 and 2× Complete Protease Inhibitors was added and the liver was homogenized using an Ultraturrax and a Potter-Elvehjem homogenizer, followed by centrifugation at 10,000×g for 10 min at 4° C. The resultant supernatant was slowly stirred at room temperature for 60 min, then again centrifuged at 100,000×g for 90 min at 4° C. The supernatant was then applied to an agarose-bound wheat germ agglutinin (WGA) column. The column was washed with 50 mM Hepes (pH 7.4), 0.1% Triton X-100, and bound glycoproteins were eluted from the WGA column with this buffer containing 0.3 M N-acetylglucoseamine.

In vitro Phosphorylation Assay

For rIRS-1$^{449-664}$ phosphorylation by insulin receptor, 5 pg of the WGA-purified glycoprotein fraction was preincubated for 30 min at 30° C. with 100 nM of insulin in a phosphorylation buffer containing 20 mM Hepes (pH 7.4), 1 mM DTT, 10 mM MgCl$_2$, 100 µg/ml bovine serum albumin, 0.2 mM Na$_3$VO$_4$, 1.7 mM CaCl$_2$, 0.6 mg/ml phosphatidylserine, and 0.5 µg/ml okadaic acid. Autophosphorylation was initiated by the addition of ATP at a concentration of 50 µM and continued for 10 min at 30° C. Substrate phosphorylations were initiated by addition of equal volumes of rIRS-1$^{449-669}$ (1 µg) with or without pre-treatment (30 min) by the PKC isoforms in the same buffer in the presence of 50 µM ATP and was allowed to proceed for 10 min at 30° C. in a final volume of 50 µl. The reaction was terminated by the addition of 6× sample buffer (0.35 M Tris-HCl (pH 6.8), 10.28% (w/v) SDS, 36% (v/v) glycerol; 0.6 M DTT, 0.012% (w/v) bromphenol blue) and boiling for 5 min. Proteins were separated by SDS-PAGE and analyzed by immunodetection with an anti-phosphotyrosine antibody after transfer to nitrocellulose. Serine/threonine phosphorylation of rIRS-1$^{449-664}$ by different PKC isoforms was assessed by incubating 1 µg rIRS-1$^{449-664}$ with 0.5 µg PKC-rb or PKC-ζ in phosphorylation buffer for 30 min at 30° C. in the presence of 50 µM ATP plus 2 µCi [γ-$^{32}$P]ATP in a volume of 20 µl. Proteins were resolved by SDS-PAGE and the stained and dried gels were subjected to autoradiography. The extent of phosphate incorporation was determined by Cerenkov counting of excised fragments.

GST Pull Down Assay

In vitro phosphorylated rIRS-1$^{449-664}$ was incubated with glutathione sepharose beads on a rotator for 1 h at 4° C. Pellets were washed three times with binding buffer (50 mM Tris (pH 7.4), 150 mM NaCl, 1% (v/v) Nonidet P-40, 1 mM EDTA, 1 mM NaF, 1 mM Na$_3$VO$_4$). Then 0.5 µg recombinant p85α was added and incubation was continued for 2 h at 4° C. After three times washing, the bound proteins were eluted with 20 µl of 2× sample buffer and separated by SDS-PAGE.

Immunoblotting

Proteins were separated by SDS-PAGE using 8-18% gradient gels followed by transfer to nitrocellulose in a semi-dry blotting apparatus. The membrane was then blocked 60 min in Tris-buffered saline containing 0.05% Tween 20 and 1% BSA or 5% non fat dry milk and probed with appropriate antibodies (anti-IRS-1, anti-pTyr, anti-p85α). After extensive washing, the membranes were incubated with horseradish peroxidase-conjugated secondary antibodies, again washed and then the protein bands were visualized by the enhanced chemiluminescence (ECL) method on a Lumilmager workstation (Boehringer, Mannheim, Germany). All blots were quantified using the Lumilmager software. Significance of reported differences was evaluated by using the null hypothesis and t statistics for unpaired data. A p value less than 0.05 was considered to be statistically significant.

Phosphopeptide Mapping by High Performance Liquid Chromatography (HPLC) and Electrospray Ionisation Mass Spectrometry (ESI-MS)

Using 50 U (40 µg) of PKC-ζ, 5 nmol of rIRS-1$^{449-664}$ protein was phosphorylated with 50 µM ATP plus 0.25 mCi/ml [γ-$^{32}$P]ATP for 60 min under conditions described above. Proteins were separated by SDS-PAGE and phosphorylated rIRS-1$^{449-664}$ was digested with 100 µg trypsin in the excised gel pieces overnight at 30° C.

Peptides were eluted with 50 mM NH$_4$HCO$_3$, 50% acetonitrile and separated on an anion exchange column (Nucleogel SAX 1000-8/46, 50×4.6 mm, Macherey & Nagel, Düren, Germany) using Beckman gold solvent delivery system. The HPLC flow rate was 0.5 ml/min. After injection of sample, the peptides were eluted beginning at 100% buffer A (20 mM NH$_4$CH$_3$COOH, pH 7.0) and 0% of buffer B (1 M KH$_2$PO$_4$, pH 4.0). The amount of buffer B was increased to 10% within 40 min and from 10 to 50% during the following 75 min. Fractions of 0.5 ml were collected, and radioactivity was measured by Cerenkov counting. Radioactive fractions were subjected to reversed phase HPLC. Peptides were separated on a C18-reversed phase column (Nucleosil 300-5 C18, 250 mm×2 mm, 5 µm particle size, 300 A pore size, Macherey & Nagel, Düren, Germany). The HPLC flow rate was adjusted to 0.33 ml/min. After application of the sample, elution started with 100% of solution A (0.1% TFA) and 0% of solution B (acetonitrile/TFA (84/0.1; v/v)). The content of solution B was raised to 100% in 120 min. Again the radioactivity of the collected fractions was measured. Fractions containing radiolabeled peptides were subjected to ESI-TOF mass spectrometry. Mass spectra were recorded on an electrospray quadrupole time-of-flight mass spectrometer (QSTAR Pulsar I, Applied Biosystems, Foster City, Calif., USA) using a nanospray source (Protana, Odense, Denmark). Selected peptides were analyzed in tandem mass spectrometry mode and the sequence and posttranslational modifications were retrieved by manual interpretation.

Site-Directed Mutagenesis

The serine 570 to alanine and serine 612 to alanine mutants of rIRS-1$^{449-664}$ were generated by site-directed mutagenesis using the QuikChange™ Site-Directed Mutagenesis Kit according to the manufacturer's instructions using pGEX-5X-3/rIRS-1$^{449-664}$ as a template. The following primers were used:

S570A, (SEQ ID NO:3)
5'-CCCGGCTACCGGCATGCCGCCTTCGTGCCCACC and (SEQ ID NO:4)
3'-GGGCCGATGGCCGTACGGCGGAAGCACGGGTGG;

S612A, (SEQ ID NO:5)
5'-GGCTACATGCCCATGGCTCCCGGAGTGGCTCC and (SEQ ID NO:6)
3'-CCGATGTACGGGTACCGAGGGCCTCACCGAGG.

Presence of the desired mutations was confirmed by sequencing the recombinant molecules by Qiagen Sequencing Services (Hilden, Germany).

Interaction Studies by Surface Plasmon Resonance Technology

The principle of operation of the BIAcore™ biosensor (Biacore, Freiburg, Germany) has been described previously (42). To avoid the interfering dimerization of the GST part of the fusion protein, it was cleaved with thrombin during the purification. Because of the known extremely fast association rates of SH2-domains to phosphopeptides the relative affinities were assessed by competition assay (43). Therefore, a constant concentration of p85α (100 nM) was incubated in running buffer (0.01 M Hepes pH 7.4, 0.15 M NaCl, 3 mM EDTA, 0.005% Surfactant P20 (HBS-EP)) with a variable concentration of the competitor peptide (50 nM-10 μM), which was identical to that bound on the CM5 sensor chip surface. After a 1 h preincubation at room temperature the various mixtures were then injected sequentially at a flow rate of 5 μl/min at 25° C. in HBS-EP buffer. The used peptides DDGYMPMSPGV (SEQ ID NO: 7), DDGpYMPMSPGV, DDGYMPMpSPGV and DDGpYMPMpSPGV, representing the amino acids 605 to 615 of rat IRS-1, were synthesized on an Applied Biosystems model 433 peptide synthesizer. All peptides were immobilized with a concentration of 5 mg/ml in 100 mM $H_3BO_4$ (NaOH pH 8.5) at 1 μl/min by standard amine coupling procedure as described by the manufacturer. Regeneration after each binding experiment was performed by injection of 6 M guanidine hydrochloride for 2 min. The kinetic analysis of the p85α with pY608 and pY606-pS612 interaction has been performed using the BIAevaluation 3.1 software (Biacore, Freiburg, Germany) and GraphPad Prism 3.0 (San Diego, Calif., USA).

Measurement of Serine/threonine phosphorylation of rIRS-$1^{449}$-664 by PKC Serine/threonine phosphorylation of rIRS-$1^{449-664}$ by different PKC isoforms was assessed by pipetting appropriate volumes of 1 μg rIRS-$1^{449-664}$ and 0.1-1.0 μg PKC-ζ or PKC-rat brain into μl 2× phosphorylation buffer (20 mM Hepes (pH 7.4), 1 mM DTT, 10 mM $MgCl_2$, 100 μg/ml bovine serum albumin, 0.2 mM $Na_3NO_4$, 1.7 mM $CaCl_2$, 0.6 mg/ml phosphatidylserine, and 0.5 μg/ml okadaic acid, 50 μM ATP+2 μCi [γ-$^{32}$P]ATP). The mixture was adjusted with water to an end volume of 20 μl minus the necessary ATP volume. Then the phosphorylation reaction was started by addition of ATP from a stock solution to an end concentration of 50 μM ATP plus 2 μCi [γ-$^{32}$P]ATP and incubated for 30 min at 30° C. The reaction was stopped by addition of 4 μl 6× sample buffer (0.35 M Tris-HCl (pH 6.8), 10.28% (w/v) SDS, 36% (v/v) glycerol; 0.6 M DTT, 0.012% (w/v) bromphenol blue) and boiling for 5 min. The proteins were then resolved by SDS-Page and the stained and dried gels were subjected for analysis to autoradiography.

Example 3

Figure 1:
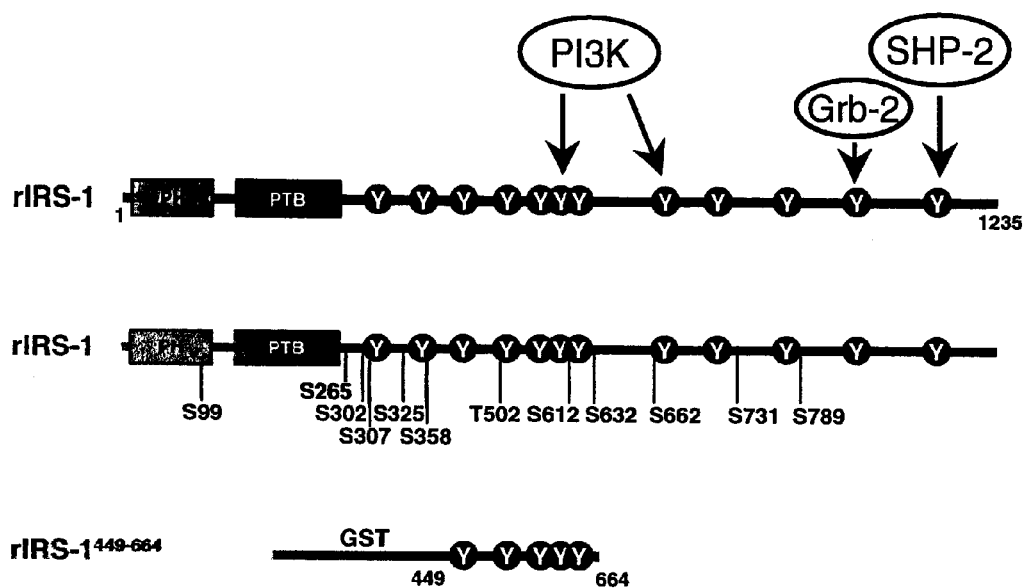
FIG. 1: Schematic overview of IRS-1 with known interaction partners and known serine/threonine phosphorylation sites.

An IRS-1 Domain is Phosphorylated by the Insulin Receptor and Interacts with PI 3-Kinase In order to determine the effects of serine/threonine phosphorylation on the interaction of IRS-1 with the insulin receptor and PI3-kinase, the inventors developed an in vitro phosphorylation and PI 3-kinase interaction assay using recombinant p85α and a GST-pulldown approach. A selected part of the rat IRS-1 protein was cloned, expressed as a GST-fusion protein and purified from *E. coli*. This GST-fusion protein (rIRS-$1^{449-664}$) covers a domain of 216 amino acids (449-664) of the rat IRS-1 protein containing potential tyrosine phosphorylation sites within YMXM or YXXM consensus motifs, including the major PI3-kinase binding sites Tyr608 and Tyr628 (39) (see FIG. 1). Based on the structure of the coded fusion protein a molecular mass of 51.2 kDa was calculated, an apparent weight of 55 kDa was determined by SDS-PAGE. The experimental procedure of the in vitro phosphorylation and p85α interaction assay is presented in FIG. 2A.

Exposing the fusion protein to WGA-purified insulin receptor induced to a prominent insulin-stimulated tyrosine phosphorylation of rIRS-$1^{449-664}$ (FIG. 2B, upper panel). Quantification showed an 8.8±1.1 fold stimulation over basal (n=10, FIG. 2C). The GST-pulldown assay revealed a significant increase in the interaction of the p85α regulatory subunit of PI3-kinase with the tyrosine phosphorylated rIRS-$1^{449-664}$ (FIG. 2B, middle panel).

Example 4

Different PKC Isoforms Inhibit Insulin-Stimulated Tyrosine Phosphorylation of rIRS-$1^{449-664}$ and subsequent association to p85α

In order to assess if protein kinase C is capable of phosphorylating rIRS-$1^{449-664}$ in vitro, the inventors first incubated the fusion protein with PKC rat brain and PKC-ζ in the presence of [$^{32}$P]ATP. rIRS-$1^{449-664}$ was then analyzed by SDS-PAGE and autoradiography (FIG. 3A) and a prominent phosphorylation of rIRS-$1^{449-664}$ by PKC became detectable. rIRS-$1^{449-664}$ incubated with the same amount of PKC in the presence of PKC inhibitors exhibited no significant incorporation of phosphate (FIG. 3A). A dose-response curve with increasing amounts of PKC was then determined to establish conditions of max. phosphorylation, which was observed with 0.5 μg PKC rat brain or PKC-ζ (data not shown). Using this condition the inventors then investigated the influence of the serine phosphorylation of rIRS-$1^{449-664}$ on the subsequent activation by the autophosphorylated IR. Therefore, rIRS-$1^{449-664}$ was treated with or without PKC and then incubated with WGA-purified IR. p85α association was subsequently determined by coupling rIRS-$1^{449-664}$ to glutathione sepharose beads via its GST part and incubation with 0.5 pg p85α, as outlined in FIG. 2A. Samples were analyzed by SDS-PAGE and immunoblotting with antibodies against phosphotyrosine (pTyr), p85α, and IRS-1. As shown in FIG. 3B, pretreatment of rIRS-$1^{449-664}$ with PKC rat brain caused a decrease in the insulin-stimulated tyrosine phosphorylation and the interaction with p85α. Tyr-phosphorylation of rIRS-$1^{449-664}$ was reduced by 27±4% (n=9) with a more prominent inhibition of the association of p85α (49±8%) (FIG. 3C). Inhibition of PKC-rb after phosphorylation of rIRS-$1^{449-664}$ by addition of bisindolylmaleimide (BIM) did not modify this result (FIG. 3C).

To further exclude effects of PKC at the level of IR, the autophosphorylation of the β-subunit was examined. No significant alteration of IR autophosphorylation became detectable when the autoactivated receptor was incubated for 10 min at 30° C. in the presence of PKC-rb or PKC-ζ when compared to controls (FIG. 4).

The experimental approach described in FIG. 3B was then repeated for PKC-ζ. When compared to PKC-rb, an even more prominent reduction in the tyrosine phosphorylation of rIRS-$1^{449-664}$ and interaction with p85α was observed (FIG. 5A). Quantification of the data showed an inhibition of tyrosine phosphorylation by 46±5% (n=3) and a concomitant inhibition of p85α binding to IRS-1 by 81±1% (FIG. 5B).

Example 5

Identification and Functional Analysis of IRS-1 Serine Phosphorylation Sites Targeted by PKC Prior studies have indicated that negative regulation of insulin signaling by protein kinase C involves the mitogen-activated protein kinase and phosphorylation of serine 612 in IRS-1 (26). Serine 612 is localized in direct neighborhood to a major YMXM motif at Y608 which is described to be one of the main interaction sites for PI 3-kinase (39).

The inventors assessed modification of this site by PKC using a specific IRS-1 phosphoserine 612 antibody (αpS$^{612}$). After incubation with PKC from rat brain and PKC-ζ for 30 min at 30° C., rIRS-1$^{449-664}$ was strongly immunoblotted with αpS$^{612}$ (FIG. 6A); inhibition of PKC with BIM clearly prevented the phosphorylation of this serine.

To characterize the influence of phosphoserine 612 of IRS-1 on the interaction with PI 3-kinase the technique of surface plasmon resonance (SPR) was used. For this purpose peptides were synthesized with the sequence DDGYMPMSPGV (SEQ ID NO:7) representing amino acids 605 to 615 of rat IRS-1 and immobilized on a chip surface by standard amine coupling. It has been reported that fusion of SH2 domains to GST may affect their binding to phosphopeptides leading to an overestimation of the binding affinity (44). Therefore, the GST part of the recombinant p85α fusion protein was cleaved. Binding of p85α to the peptides was studied by applying various concentrations of the purified p85α to a biosensor chip to which the peptides were coupled in different phosphorylation forms. These experiments showed that p85α only binds to the tyrosine phosphorylated form of the peptide (FIGS. 6B and C), consistent with the literature (45).

The inventors then determined the relative binding affinity of this reaction by monitoring the binding of 100 nM p85α to the peptides pY608 (DDGpYMPMSPGV) and pY608-pS612 (DDGpYMPMpSPGV) in the presence of competing soluble peptides (FIGS. 6D, E, F). Half-maximum inhibitory concentrations (IC50) were obtained by plotting the SPR response 440 s after injection at equilibrium versus the log peptide concentration. Both peptides displayed a measurable binding activity (FIGS. 6D versus 6E). Solubilized peptides inhibited binding of p85α to the immobilized peptides at micromolar concentrations. Complete inhibition was achieved at a peptide concentration of ~10 µM. Fitting of the determined readings with an equation for two site competition resulted in an IC50 for pY608 of 0.26 µmol/l and 16.56 µmol/l ($r^2$=0.9983), and for pY608-pS612 of 0.15 µmol/l, 2.88 µmol/l ($r^2$=0.9989). From this data it is clear that the peptide pY608-pS612 inhibited the binding of p85α with a better efficiency, indicating that the presence of a phosphoserine residue at position +4 of the phosphotyrosine even increases the affinity of the p85α SH2-domain for the IRS-1 phosphopeptide. In order to identify additional PKC-ζ phosphorylation sites on rIRS-1$^{449-664}$ that might promote the inhibition of insulin-stimulated tyrosine phosphorylation in the in vitro system, rIRS-1$^{449-664}$ was incubated with PKC-ζ and separated by SDS-PAGE. Phosphorylated rIRS-1$^{449-664}$ was digested with trypsin and extracted from the gel. The peptides generated by digestion were resolved by two dimensional HPLC and the content of radioactivity in the fractions was monitored by Cerenkov counting. The HPLC profile of the first separation using an anion exchange column showed 6 reproducible major peaks (FIG. 7A). To separate comigrating peptides, radioactive fractions of each peak were pooled according to the elution profile and subjected to reversed phase (RP)-HPLC (FIG. 7B). This resulted in 10 distinct radiolabeled RP-HPLC fractions that were subsequently subjected to electrospray ionization mass spectrometry (ESI-MS). The results obtained by MS analysis are summarized in Table 1. Eight peptides could be identified, covering 37% of the rIRS-1$^{449-664}$ sequence. Two phosphoserines were found, serine 358 (serine 570 in full length IRS-1) (LPGYRHpSAFVPTHSYPEEGLEMHHLER (SEQ ID NO:8)) in peak 4 of anion exchange HPLC, and serine 286 (serine 498) (YIPGATMGTpSPALTGDEAAGAADLDNR (SEQ ID NO:9)) in peak 5 and 6. The phosphopeptide with serine 358/570 corresponded to about 19% of the incorporated radioactivity. The peptide with phosphoserine 286/498 accounted for 11% of the overall measured radioactivity.

Phosphoserine 358 was identified by ESI-MS/MS. The fragment ion with a mass difference of 97.9 Da to the parent ion indicates a phosphopeptide (FIG. 8A). A mass difference 97.9 Da correlates to the loss of phosphoric acid. The site of phosphorylation was identified by the loss of the phosphate group ($HPO_3$) and phosphoric acid ($H_3PO_4$) from the fragment ions $b_9$ and $b_{10}$. This dephosphorylation of the fragment ions indicates that the phosphorylation could only take place by the Y355 or S358. S358 is the phosphoaminoacid, because there was no dephosphorylation detected from the $b_4$ ion, indicating a phosphorylation at Y355 (data not shown).

Phosphoserine 612 could not be detected by mass spectrometry despite being detected by a phosphosite specific antibody (FIG. 6A), but a peptide including this site was found in peak 2 together with three additional peptides. Peak 1 and peak 3 contained only one peptide covering 13% and 21% of the radioactivity, respectively (THSAGTSPTISHQK and TPSQSSVVSIEEY-TEMMPAAYPPGGGSGGR). (SEQ ID NO:10 and 11)

To further confirm that the phosphorylation sites found were serine 570 and 612, two additional GST fusion proteins with mutation of serine to alanine were generated. These GST fusion proteins were exposed to PKC-ζ and were phosphorylated by the enzyme at a level comparable to the wild type (data not shown). On the other hand, converting serine 358/570 to alanine largely reduced peak 4 in anion exchange HPLC (FIG. 9B) demonstrating that serine 570 of IRS-1 is a novel phosphorylation site targeted by PKC-ζ. The serine 400/612 to alanine mutation leads to a decrease of peak 2 (FIG. 9C), confirming the data obtained with the phospho-specific antiserum.

Example 6

Functional Relevance of Serine Residues 570 and 612 in rIRS-1$^{449-664}$

To determine the functional relevance of the identified phosphosites the rIRS-1$^{449-664}$ serine 358/570 to alanine and serine 400/612 mutants were tested in the in vitro phosphorylation and p85α interaction assay (FIG. 10A). Comparing the results of tyrosine phosphorylation by IR after PKC-ζ pretreatment showed a comparable reduction (30-40%) for wild type rIRS-1$^{449-664}$ and the two mutants (FIG. 10B, left panel). However, a significant difference became apparent when comparing the interaction of the two mutants with p85α. Thus, p85α binding to S570A was reduced to 43±4% (n=3) of control by PKC-ζ treatment, with a reduction to 28±3% for the S612A mutant of rIRS-1$^{449-664}$ (FIG. 10B, right panel).

The abbreviations used are: GST, glutathione S-transferase; HPLC, high performance liquid chromatography; IR, insulin receptor; IRS, insulin receptor substrate; ESI-MS, electrospray ionization mass spectrometry; p85, regulatory subunit of phosphatidylinositol (PI)-3 kinase; PAGE, polyacrylamide gel electrophoresis; PI 3-kinase, phosphatidylinositol-3-kinase; RP, reversed phase; PKC, protein kinase C; PKB, protein kinase B; RTKs, receptor tyrosine kinases; SH2, src-homology domain 2; WGA, wheat germ agglutinine; SDS, sodium dodecyl sulphate; ECL, enhanced chemiluminescence.

TABLE 1

Sequence Analysis Results of rIRS1$^{449-664}$ Phosphopeptides

| Amino acid sequence of the identified phosphopeptide | aa in rIRS1$^{499-644b}$ | Phosphorylated residue | peak$^c$ | Part of $^{32}$P (%)$^d$ |
|---|---|---|---|---|
| VAHTPPARGEEELSNYICMGGK (SEQ ID NO:12) | 233-254 | | 4 & 2 | |
| GASTLTAPNGHYILSR (SEQ ID NO:13) | 255-270 | | 2 | 20.7 |
| YIPGATMGTSPALTGDEAAGAADLDNR (SEQ ID NO:9) | 277-303 | S286 | 5 & 6 | 10.6 |
| THSAGTSPTISHQK (SEQ ID NO:10) | 308-321 | | 1 | 12.9 |
| TPSQSSVVSIEEYTEMMPAAYPPGGGSGGR (SEQ ID NO:11) | 322-351 | | 3 | 21.2 |
| LPGYRHSAFVPTHSYPEEGLEMHHLER (SEQ ID NO:8) | 352-378 | S358 | 4 | 18.8 |
| GGHHRPDSSNLHTDDGYMPMSPGVAPVPSNR (SEQ ID NO:14) | 380-410 | | 2 | 20.7 |
| VDPNGYMMMSPSAAAS (SEQ ID NO:15) | 441-456 | | 2 | 20.7 |

$^a$Tryptic peptides of rIRS-1$^{449-664}$ were analyzed after anion exchange HPLC and reversed phase HPLC by mass spectrometry. Phosphorylated serine residues are marked in bold letters.
$^b$Numbering according to a composed sequence of glutathione S-transferase plus IRS-1 amino acids 449-664.
$^c$Peaks from anion exchange chromatography HPLC (numbers) (see FIGURE 7 A).
$^d$Total amount of radioactivity incorporated into the identified phosphopeptides was set as 100% and the percentage given represents the integrated peak area.

REFERENCES

1. White, M. F. (1998) *Mol. Cell. Biochem.* 182, 3-11
2. Thirone A C, Carvalho C R, Saad M J. (1999) *Endocrinology* 140, 55-62
3. Cheatham, B., and Kahn, C. R. (1995) *Endocr. Rev.* 16,117-142
4. Backer, J. M., Myers, M. G. Jr., Shoelson, S. E., Chin, D. J., Sun, X. J., Miralpeix, M., Hu, P., Margolis, B., Skolnik, E. Y., and Schlessinger, J. (1992) *EMBO J.* 11, 3469-3479
5. Skolnik, E. Y., Lee, C. H., Batzer, A., Vicentini, L. M., Zhou, M., Daly, R., Myers, M. J. Jr., Backer, J. M., Ulirich, A., and White, M. F. (1993) *EMBO J.* 12,1929-1936
6. Sun, X. J., Crimmins, D. L., Myers, M. G. Jr., Miralpeix, M., and White, M. F. (1993) *Mol. Cell. Biol.* 13, 7418-7428
7. Shepherd, P. R., Withers, D. J., and Siddle, K. (1998) *Biochem. J.* 333, 471-490
8. Alessi, D. R., and Cohen, P. (1998) *Curr. Opin. Genet Dev.* 8, 55-62
9. Lawlor, M. A., and Alessi, D. R. (2001) *J. Cell. Sci.* 114, 2903-2910
10. Bandyopadhyay, G., Sajan, M. P., Kanoh, Y., Standaert, M. L., Quon, M. J., Reed, B. C., Dikic, I., and Farese, R. V. (2001) *J. Biol. Chem.* 276, 35537-35545
11. Bandyopadhyay, G., Sajan, M. P., Kanoh, Y., Standaert, M. L., Quon, M. J., Lea-Currie, R., Sen, A., and Farese, R. V. (2002) *J. Clin. Endocrinol. Metab.* 87, 716-723
12. Summers, S. A., Kao, A. W., Kohn, A. D., Backus, G. S., Roth, R. A., Pessin, J. E., and Birnbaum, M. J. (1999) *J. Biol. Chem.* 274, 17934-17940
13. Kitamura, T., Kitamura, Y., Kuroda, S., Hino, Y., Ando, M., Kotani, K., Konishi, H., Matsuzaki, H., Kikkawa, U., Ogawa, W., and Kasuga, M. (1999) *Mol. Cell. Biol.* 19, 6286-6296.
14. Eriksson, H., Ridderstrale, M., Degerman, E., Ekholm, D., Smith, C. J., Manganiello, V. C., Belfrage, P., and Tornqvist, H. (1995) *Biochim. Biophys. Acta.* 1266, 101-107
15. Nave, B. T., Ouwens, M., Withers, D. J., Alessi, D. R., and Shepherd, P. R. (1999) *Biochem. J.* 344, 427-431
16. Scott, P. H., Brunn, G. J., Kohn, A. D., Roth, R. A., and Lawrence, J. C. Jr. (1998) *Proc. Natl. Acad. Sci.* 95, 7772-7777
17. White, M. F. (2002) *Am. J. Physiol. Endocrinol. Metab.* 283, E413-422
18. Birnbaum, M. J. (2001) *J. Clin. Invest.* 108, 655-659
19. Zick, Y. (2001) *Trends Cell. Biol.* 11, 437-441
20. Tanti, J. F., Gremeaux, T., van Obberghen, E., and Le Marchand-Brustel, Y. (1994) *J. Biol. Chem.* 269, 6051-6057
21. Sun, X. J., Rothenberg, P., Kahn, C. R., Backer, J. M., Araki, E., Wilden, P. A., Cahill, D. A., Goldstein, B. J., and White, M. F. (1991) *Nature* 352, 73-77

22. Hotamisligil, G. S., Peraldi, P., Budavari, A., Ellis, R., White, M. F., and Spiegelman, B. M. (1996) *Science* 271, 665-668
23. Shulman, G. I. (2000) *J. Clin. Invest.* 106, 171-176
24. Virkamaki, A., Ueki, K., and Kahn, C. R. (1999) *J. Clin. Invest.* 103, 931-943
25. Aguirre, V., Werner, E. D., Giraud, J., Lee, Y. H., Shoelson, S. E., and White, M. F. (2002) *J. Biol. Chem.* 277, 1531-1537
26. Gao, Z., Hwang, D., Bataille, F., Lefevre, M., York, D., Quon, M. J., and Ye, J. (2002) *J. Biol. Chem.* 277, 48115-48121
27. De Fea, K., and Roth, R. A. (1997) *J. Biol. Chem.* 272, 31400-31406
28. Tanasijevic M J, Myers M G Jr, Thoma R S, Crimmins D L, White M F, Sacks D B. (1993) *J. Biol. Chem.* 268, 18157-18166
29. Eldar-Finkelman H, Krebs E G. (1997) *Proc. Natl. Acad. Sci. USA* 94, 9660-9664
30. Freund G G, Wittig J G, Mooney R A. (1995) *Biochem Biophys Res Commun* 206, 272-278
31. Sun X J, Rothenberg P, Kahn C R, Backer J M, Araki E, Wilden P A, Cahill D A, Goldstein B J, White M F. (1991) *Nature* 352, 73-77
32. Schmitz-Peiffer C, Craig D L, Biden T J. (2002) *Ann. N.Y. Acad. Sci.* 967, 146-157
33. Paz, K., Liu, Y. F., Shorer, H., Hemi, R., LeRoith, D., Quan, M., Kanety, H., Seger, R., and Zick, Y. (1999) *J. Biol. Chem.* 274, 28816-28822
34. Jakobsen, S. N., Hardie, D. G., Morrice, N., and Tornqvist, H. E. (2001) *J. Biol. Chem.* 276, 46912-46916
35. Greene, M. W., and Garofalo, R. S. (2002) *Biochemistry* 41, 7082-7091
36. Lee, Y. H., Giraud, J., Davis, R. J., and White, M. F. (2003) *J. Biol. Chem.* 278, 2896-2902
37. Qiao, L. Y., Zhande, R., Jetton, T. L., Zhou, G., and Sun, X. J. (2002) *J. Biol. Chem.* 277, 26530-26539
38. Mothe, I., and Van Obberghen, E. (1996) *J. Biol. Chem.* 271, 11222-11227
39. DeFea, K., and Roth, R. A. (1997) *Biochemistry* 36, 12939-12947
40. Li, J., DeFea, K., and Roth, R. A. (1999) *J. Biol. Chem.* 274, 9351-9356
41. Braiman, L., Alt, A., Kuroki, T., Ohba, M., Bak, A., Tennenbaum, T., and Sampson, S. R. (2001) *Mol. Cell. Biol.* 21, 7852-7861
42. Standaert, M. L., Ortmeyer, H. K., Sajan, M. P., Kanoh, Y., Bandyopadhyay, G., Hansen, B. C., and Farese, R. V. (2002) *Diabetes* 51, 2936-2943
43. Ravichandran, L. V., Esposito, D. L., Chen, J., and Quon, M. J. (2001) *J. Biol. Chem.* 276, 3543-3549
44. Liu, Y. F., Paz, K., Herschkovitz, A., Alt, A., Tennenbaum, T., Sampson, S. R., Ohba, M., Kuroki, T., LeRoith, D., and Zick, Y. (2001) *J. Biol. Chem.* 276, 14459-14465
39. Esposito, D. L., Li, Y., Cama, A., and Quon, M. J. (2001) *Endocrinology* 142, 2833-2840
40. Smith, D. B., and Johnson, K. S. (1988) *Gene* 67, 31-40
41. Burant, C. F., Treutelaar, M. K., Landreth, G. E., and Buse, M. G. (1984) *Diabetes* 33, 704-708
42. Malmqvist, M., and Karlsson, R. (1997) *Curr. Opin. Chem. Biol.* 1, 378-383
43. Vely, F., Trautmann, A., and Vivier, E. (2000) *Methods Mol. Biol.* 121, 313-21
44. Ladbury, J. E., Lemmon, M. A., Zhou, M., Green, J., Botfield, M. C., and Schlessinger, J. (1995) *Proc. Natl. Acad. Sci. U.S.A.* 92, 3199-203
45. Felder, S., Zhou, M., Hu, P., Urena, J., Ullrich, A., Chaudhuri, M., White, M., Shoelson, S. E., and Schiessinger, J. (1993) *Mol. Cell. Biol.* 13, 1449-55

The invention claimed is:

1. A method for identifying an IRS protein kinase inhibitor, the method comprising the steps of
   a) contacting, in the presence of at least one possible inhibitor, PKC-ζ with at least one IRS peptide comprising amino acid sequence of SEQ ID NO:17 comprising at least one PKC-ζ-Ser-phosphorylation site, and
   b) measuring the phosphorylation of a PKC-ζ-Ser-phosphorylation site at a residue selected from the group consisting of residues 498, 570, and 612, wherein phosphorylation at one or more of residues 498, 570 or 612 inhibits insulin-stimulated tyrosine phosphorylation of the IRS peptide or inhibits interaction of p85α regulatory subunit of phosphatidylinositol 3-kinase with the IRS peptide.

2. The method of claim 1, wherein a reduced phosphorylation of the PKC-ζ-Ser-phosphorylation site compared to the phosphorylation in the absence of the at least one possible inhibitor is indicative for the inhibitory properties of the possible inhibitor.

3. The method of claim 1, wherein the PKC-ζ is of mammalian origin.

4. The method of claim 3, wherein the PKC-ζ is of human or rodent origin.

5. The method of claim 4, wherein the PKC-ζ is of rat origin.

6. The method of claim 1, wherein the possible inhibitor is selected from the group consisting of antibodies, binding peptides, and low molecular weight compounds.

* * * * *

UNITED STATES PATENT AND TRADEMARK OFFICE
CERTIFICATE OF CORRECTION

| | | |
|---|---|---|
| PATENT NO. | : 7,803,571 B2 | |
| APPLICATION NO. | : 10/918015 | |
| DATED | : September 28, 2010 | |
| INVENTOR(S) | : Norbert Tennagels et al. | |

It is certified that error appears in the above-identified patent and that said Letters Patent is hereby corrected as shown below:

Title Pg, Item (75), in column 1, in "Inventors", line 2, delete "Erkath" and insert -- Erkrath --, therefor.

Title Pg, Item (73), in column 1, in "Assignee", line 19, delete "Sanfoi" and insert -- Sanofi --, therefor.

Title Pg, Item (56), in column 2, under "Other Publications", line 1, delete "Insuling" and insert -- Insulin --, therefor.

Title Pg, Item (56), in column 2, under "Other Publications", line 11, delete "Phosphlipase" and insert -- Phospholipase --, therefor.

Title Pg, Item (56), in column 2, under "Other Publications", line 17, delete "insuling" and insert -- insulin --, therefor.

Title Pg, Item (56), in column 2, under "Other Publications", line 48, delete "P13-Kinase," and insert -- PI 3-Kinase, --, therefor.

Title Pg. 2, Item (56), in column 1, under "Other Publications", line 5, delete "Insuling" and insert -- Insulin --, therefor.

Title Pg. 2, Item (56), in column 1, under "Other Publications", line 18, delete "Theonine" and insert -- Threonine --, therefor.

Title Pg. 2, Item (56), in column 1, under "Other Publications", line 33, delete "Van-Fang" and insert -- Yan-Fang --, therefor.

Title Pg. 2, Item (56), in column 2, under "Other Publications", line 15, delete "at al.," and insert -- et al., --, therefor.

Signed and Sealed this
Twenty-fifth Day of January, 2011

David J. Kappos
*Director of the United States Patent and Trademark Office*

CERTIFICATE OF CORRECTION (continued)
U.S. Pat. No. 7,803,571 B2

In column 2, line 22, delete "$Ser^{739}$" and insert -- $Ser^{789}$ --, therefor.

In column 4, line 4, delete "5,10," and insert -- 5, 10, --, therefor.

In column 4, line 5, delete "50,100," and insert -- 50, 100, --, therefor.

In column 4, line 24, delete "phosphopeptid" and insert -- phosphopeptide --, therefor.

In column 5, line 28, after "New York)" insert -- . --.

In column 5, line 64, delete "$rIRS^{449-664}$" and insert -- $rIRS\text{-}1^{449-664}$ --, therefor.

In column 6, line 5, after "IRS" insert -- . --.

In column 6, line 22, delete "thereol" and insert -- thereof, --, therefor.

In column 6, line 29, delete "arc" and insert -- are --, therefor.

In column 13, line 37, delete "$rIRS\text{-}1^{1449}\text{-}664$" and insert -- $rIRS\text{-}1^{449-664}$ --, therefor.

In column 13, line 63, delete "P13-kinase," and insert -- PI 3-kinase, --, therefor.

In column 20, line 35, delete "Schiessinger," and insert -- Schlessinger, --, therefor.

SEQUENCE LISTING

<160> NUMBER OF SEQ ID NOS: 17

<210> SEQ ID NO 1
<211> LENGTH: 29
<212> TYPE: DNA
<213> ORGANISM: artificial sequence
<220> FEATURE:
<223> OTHER INFORMATION: Primer

<400> SEQUENCE: 1
atattgtcga ccacacccca ccagccagg                                    29

<210> SEQ ID NO 2
<211> LENGTH: 37
<212> TYPE: DNA
<213> ORGANISM: artificial sequence
<220> FEATURE:
<223> OTHER INFORMATION: Primer

<400> SEQUENCE: 2
atgtactact acagagggtc acgccggcgt aagaata                           37

<210> SEQ ID NO 3
<211> LENGTH: 33
<212> TYPE: DNA
<213> ORGANISM: artificial sequence
<220> FEATURE:

-continued

```
<223> OTHER INFORMATION: Primer

<400> SEQUENCE: 3
cccggctacc ggcatgccgc cttcgtgccc acc                              33

<210> SEQ ID NO 4
<211> LENGTH: 33
<212> TYPE: DNA
<213> ORGANISM: artificial sequence
<220> FEATURE:
<223> OTHER INFORMATION: Primer

<400> SEQUENCE: 4
gggccgatgg ccgtacggcg aagcacggg tgg                               33

<210> SEQ ID NO 5
<211> LENGTH: 32
<212> TYPE: DNA
<213> ORGANISM: artificial sequence
<220> FEATURE:
<223> OTHER INFORMATION: Primer

<400> SEQUENCE: 5
ggctacatgc ccatggctcc cggagtggct cc                               32

<210> SEQ ID NO 6
<211> LENGTH: 32
<212> TYPE: DNA
<213> ORGANISM: artificial sequence
<220> FEATURE:
<223> OTHER INFORMATION: Primer

<400> SEQUENCE: 6
ccgatgtacg ggtaccgagg gcctcaccga gg                               32

<210> SEQ ID NO 7
<211> LENGTH: 11
<212> TYPE: PRT
<213> ORGANISM: artificial sequence
<220> FEATURE:
<223> OTHER INFORMATION: Rat IRS-1 fragment

<400> SEQUENCE: 7

Asp Asp Gly Tyr Met Pro Met Ser Pro Gly Val
1               5                   10

<210> SEQ ID NO 8
<211> LENGTH: 27
<212> TYPE: PRT
<213> ORGANISM: artificial sequence
<220> FEATURE:
<223> OTHER INFORMATION: Rat IRS-1 fragment

<400> SEQUENCE: 8

Leu Pro Gly Tyr Arg His Ser Ala Phe Val Pro Thr His Ser Tyr Pro
1               5                   10                  15
Glu Glu Gly Leu Glu Met His His Leu Glu Arg
            20                  25

<210> SEQ ID NO 9
<211> LENGTH: 27
<212> TYPE: PRT
<213> ORGANISM: artificial sequence
<220> FEATURE:
<223> OTHER INFORMATION: Rat IRS-1 fragment
```

-continued

```
<400> SEQUENCE: 9

Tyr Ile Pro Gly Ala Thr Met Gly Thr Ser Pro Ala Leu Thr Gly Asp
1               5                   10                  15

Glu Ala Ala Gly Ala Ala Asp Leu Asp Asn Arg
            20                  25

<210> SEQ ID NO 10
<211> LENGTH: 14
<212> TYPE: PRT
<213> ORGANISM: artificial sequence
<220> FEATURE:
<223> OTHER INFORMATION: Rat IRS-1 fragment

<400> SEQUENCE: 10

Thr His Ser Ala Gly Thr Ser Pro Thr Ile Ser His Gln Lys
1               5                   10

<210> SEQ ID NO 11
<211> LENGTH: 30
<212> TYPE: PRT
<213> ORGANISM: artificial sequence
<220> FEATURE:
<223> OTHER INFORMATION: Rat IRS-1 fragment

<400> SEQUENCE: 11

Thr Pro Ser Gln Ser Ser Val Val Ser Ile Glu Glu Tyr Thr Glu Met
1               5                   10                  15

Met Pro Ala Ala Tyr Pro Pro Gly Gly Gly Ser Gly Gly Arg
            20                  25                  30

<210> SEQ ID NO 12
<211> LENGTH: 22
<212> TYPE: PRT
<213> ORGANISM: artificial sequence
<220> FEATURE:
<223> OTHER INFORMATION: Rat IRS-1 fragment

<400> SEQUENCE: 12

Val Ala His Thr Pro Pro Ala Arg Gly Glu Glu Glu Leu Ser Asn Tyr
1               5                   10                  15

Ile Cys Met Gly Gly Lys
            20

<210> SEQ ID NO 13
<211> LENGTH: 16
<212> TYPE: PRT
<213> ORGANISM: artificial sequence
<220> FEATURE:
<223> OTHER INFORMATION: Rat IRS-1 fragment

<400> SEQUENCE: 13

Gly Ala Ser Thr Leu Thr Ala Pro Asn Gly His Tyr Ile Leu Ser Arg
1               5                   10                  15

<210> SEQ ID NO 14
<211> LENGTH: 31
<212> TYPE: PRT
<213> ORGANISM: artificial sequence
<220> FEATURE:
<223> OTHER INFORMATION: Rat IRS-1 fragment

<400> SEQUENCE: 14

Gly Gly His His Arg Pro Asp Ser Ser Asn Leu His Thr Asp Asp Gly
1               5                   10                  15
```

<210> SEQ ID NO 15
<211> LENGTH: 16
<212> TYPE: PRT
<213> ORGANISM: artificial sequence
<220> FEATURE:
<223> OTHER INFORMATION: Rat IRS-1 fragment

<400> SEQUENCE: 15

```
Val Asp Pro Asn Gly Tyr Met Met Met Ser Pro Ser Ala Ala Ala Ser
1               5                   10                  15
```

<210> SEQ ID NO 16
<211> LENGTH: 1235
<212> TYPE: PRT
<213> ORGANISM: rat

<400> SEQUENCE: 16

```
Met Ala Ser Pro Pro Asp Thr Asp Gly Phe Ser Asp Val Arg Lys Val
1               5                   10                  15

Gly Tyr Leu Arg Lys Pro Lys Ser Met His Lys Arg Phe Phe Val Leu
                20                  25                  30

Arg Ala Ala Ser Glu Ala Gly Gly Pro Ala Arg Leu Glu Tyr Tyr Glu
                35                  40                  45

Asn Glu Lys Lys Trp Arg His Lys Ser Ser Ala Pro Lys Arg Ser Ile
                50                  55                  60

Pro Leu Glu Ser Cys Phe Asn Ile Asn Lys Arg Ala Asp Ser Lys Asn
65                  70                  75                  80

Lys His Leu Val Ala Leu Tyr Thr Arg Asp Glu His Phe Ala Ile Ala
                85                  90                  95

Ala Asp Ser Glu Ala Glu Gln Asp Ser Trp Tyr Gln Ala Leu Leu Gln
                100                 105                 110

Leu His Asn Arg Ala Lys Ala His His Asp Gly Ala Gly Gly Gly Cys
                115                 120                 125

Gly Gly Ser Cys Ser Gly Ser Ser Gly Val Gly Glu Ala Gly Glu Asp
        130                 135                 140

Leu Ser Tyr Asp Thr Gly Pro Gly Pro Ala Phe Lys Glu Val Trp Gln
145                 150                 155                 160

Val Ile Leu Lys Pro Lys Gly Leu Gly Gln Thr Lys Asn Leu Ile Gly
                165                 170                 175

Ile Tyr Arg Leu Cys Leu Thr Ser Lys Thr Ile Ser Phe Val Lys Leu
                180                 185                 190

Asn Ser Glu Ala Ala Ala Val Val Leu Gln Leu Met Asn Ile Arg Arg
                195                 200                 205

Cys Gly His Ser Glu Asn Phe Phe Phe Ile Glu Val Gly Arg Ser Ala
                210                 215                 220

Val Thr Gly Pro Gly Glu Phe Trp Met Gln Val Asp Asp Ser Val Val
225                 230                 235                 240

Ala Gln Asn Met His Glu Thr Ile Leu Glu Ala Met Arg Ala Met Ser
                245                 250                 255

Asp Glu Phe Arg Pro Arg Thr Lys Ser Gln Ser Ser Ser Ser Cys Ser
                260                 265                 270

Asn Pro Ile Ser Val Pro Leu Arg Arg His His Leu Asn Asn Pro Pro
                275                 280                 285

Pro Ser Gln Val Gly Leu Thr Arg Arg Ser Arg Thr Glu Ser Ile Thr
```

```
            290                 295                 300
Ala Thr Ser Pro Ala Ser Met Val Gly Gly Lys Pro Gly Ser Phe Arg
305                 310                 315                 320

Val Arg Ala Ser Ser Asp Gly Glu Gly Thr Met Ser Arg Pro Ala Ser
                325                 330                 335

Val Asp Gly Ser Pro Val Ser Pro Ser Thr Asn Arg Thr His Ala His
                340                 345                 350

Arg His Arg Gly Ser Ser Arg Leu His Pro Pro Leu Asn His Ser Arg
                355                 360                 365

Ser Ile Pro Met Pro Ser Ser Arg Cys Ser Pro Ser Ala Thr Ser Pro
370                 375                 380

Val Ser Leu Ser Ser Ser Ser Thr Ser Gly His Gly Ser Thr Ser Asp
385                 390                 395                 400

Cys Leu Phe Pro Arg Arg Ser Ser Ala Ser Val Ser Gly Ser Pro Ser
                405                 410                 415

Asp Gly Gly Phe Ile Ser Ser Asp Glu Tyr Gly Ser Ser Pro Cys Asp
                420                 425                 430

Phe Arg Ser Ser Phe Arg Ser Val Thr Pro Asp Ser Leu Gly His Thr
                435                 440                 445

Pro Pro Ala Arg Gly Glu Glu Glu Leu Ser Asn Tyr Ile Cys Met Gly
450                 455                 460

Gly Lys Gly Ala Ser Thr Leu Thr Ala Pro Asn Gly His Tyr Ile Leu
465                 470                 475                 480

Ser Arg Gly Gly Asn Gly His Arg Tyr Ile Pro Gly Ala Thr Met Gly
                485                 490                 495

Thr Ser Pro Ala Leu Thr Gly Asp Glu Ala Ala Gly Ala Ala Asp Leu
                500                 505                 510

Asp Asn Arg Phe Arg Lys Arg Thr His Ser Ala Gly Thr Ser Pro Thr
                515                 520                 525

Ile Ser His Gln Lys Thr Pro Ser Gln Ser Ser Val Val Ser Ile Glu
530                 535                 540

Glu Tyr Thr Glu Met Met Pro Ala Ala Tyr Pro Pro Gly Gly Gly Ser
545                 550                 555                 560

Gly Gly Arg Leu Pro Gly Tyr Arg His Ser Ala Phe Val Pro Thr His
                565                 570                 575

Ser Tyr Pro Glu Glu Gly Leu Glu Met His His Leu Glu Arg Arg Gly
                580                 585                 590

Gly His His Arg Pro Asp Ser Ser Asn Leu His Thr Asp Asp Gly Tyr
                595                 600                 605

Met Pro Met Ser Pro Gly Val Ala Pro Val Pro Ser Asn Arg Lys Gly
610                 615                 620

Asn Gly Asp Tyr Met Pro Met Ser Pro Lys Ser Val Ser Ala Pro Gln
625                 630                 635                 640

Gln Ile Ile Asn Pro Ile Arg Arg His Pro Gln Arg Val Asp Pro Asn
                645                 650                 655

Gly Tyr Met Met Met Ser Pro Ser Gly Ser Cys Ser Pro Asp Ile Gly
                660                 665                 670

Gly Gly Ser Cys Ser Ser Ser Ile Ser Ala Ala Pro Ser Gly Ser
                675                 680                 685

Ser Tyr Gly Lys Pro Trp Thr Asn Gly Val Gly Gly His Thr His
                690                 695                 700

Ala Leu Pro His Ala Lys Pro Pro Val Glu Ser Gly Gly Gly Lys Leu
705                 710                 715                 720
```

```
Leu Pro Cys Thr Gly Asp Tyr Met Asn Met Ser Pro Val Gly Asp Ser
            725                 730                 735

Asn Thr Ser Ser Pro Ser Glu Cys Tyr Tyr Gly Pro Glu Asp Pro Gln
            740                 745                 750

His Lys Pro Val Leu Ser Tyr Tyr Ser Leu Pro Arg Ser Phe Lys His
            755                 760                 765

Thr Gln Arg Pro Gly Glu Pro Glu Gly Ala Arg His Gln His Leu
770                 775                 780

Arg Leu Ser Ser Ser Gly Arg Leu Arg Tyr Thr Ala Thr Ala Glu
785                 790                 795                 800

Asp Ser Ser Ser Thr Ser Asp Ser Leu Gly Gly Tyr Cys
            805                 810                 815

Gly Ala Arg Pro Glu Ser Ser Val Thr His Pro His His Ala Leu
            820                 825                 830

Gln Pro His Leu Pro Arg Lys Val Asp Thr Ala Ala Gln Thr Asn Ser
            835                 840                 845

Arg Leu Ala Arg Pro Thr Arg Leu Ser Leu Gly Asp Pro Lys Ala Ser
850                 855                 860

Thr Leu Pro Arg Val Arg Glu Gln Gln Gln Gln Gln Gln Gln Gln Gln
865                 870                 875                 880

Gln Ser Ser Leu His Pro Pro Glu Pro Lys Ser Pro Gly Glu Tyr Val
            885                 890                 895

Asn Ile Glu Phe Gly Ser Gly Gln Pro Gly Tyr Leu Ala Gly Pro Ala
            900                 905                 910

Thr Ser Arg Ser Ser Pro Ser Val Arg Cys Leu Pro Gln Leu His Pro
            915                 920                 925

Ala Pro Arg Glu Glu Thr Gly Ser Glu Glu Tyr Met Asn Met Asp Leu
            930                 935                 940

Gly Pro Gly Arg Arg Ala Thr Trp Gln Glu Ser Gly Gly Val Glu Leu
945                 950                 955                 960

Gly Arg Val Gly Pro Ala Pro Pro Gly Ala Ala Ser Ile Cys Arg Pro
            965                 970                 975

Thr Arg Ser Val Pro Asn Ser Arg Gly Asp Tyr Met Thr Met Gln Ile
            980                 985                 990

Gly Cys Pro Arg Gln Ser Tyr Val Asp Thr Ser Pro Val Ala Pro Val
            995                 1000                1005

Ser Tyr Ala Asp Met Arg Thr Gly Ile Ala Ala Glu Lys Val Ser
    1010                1015                1020

Leu Pro Arg Thr Thr Gly Ala Ala Pro Pro Ser Ser Thr Ala
    1025                1030                1035

Ser Ala Ser Ala Ser Val Thr Pro Gln Gly Ala Ala Glu Gln Ala
    1040                1045                1050

Ala His Ser Ser Leu Leu Gly Gly Pro Gln Gly Pro Gly Gly Met
    1055                1060                1065

Ser Ala Phe Thr Arg Val Asn Leu Ser Pro Asn His Asn Gln Ser
    1070                1075                1080

Ala Lys Val Ile Arg Ala Asp Thr Gln Gly Cys Arg Arg Arg His
    1085                1090                1095

Ser Ser Glu Thr Phe Ser Ala Pro Thr Arg Ala Ala Asn Thr Val
    1100                1105                1110

Ser Phe Gly Ala Gly Ala Ala Gly Gly Gly Ser Gly Gly Gly Ser
    1115                1120                1125
```

```
Glu Asp Val Lys Arg His Ser Ser Ala Ser Phe Glu Asn Val Trp
    1130                1135                1140

Leu Arg Pro Gly Asp Leu Gly Gly Ala Ser Lys Glu Ser Ala Pro
    1145                1150                1155

Gly Cys Gly Ala Ala Gly Leu Glu Lys Ser Leu Asn Tyr Ile
    1160                1165                1170

Asp Leu Asp Leu Val Lys Asp Val Lys Gln His Pro Gln Asp Cys
    1175                1180                1185

Pro Ser Gln Gln Gln Ser Leu Pro Pro Pro Pro His Gln Pro
    1190                1195                1200

Leu Gly Ser Asn Glu Gly Ser Ser Pro Arg Arg Ser Ser Glu Asp
    1205                1210                1215

Leu Ser Thr Tyr Ala Ser Ile Asn Phe Gln Lys Gln Pro Glu Asp
    1220                1225                1230

Arg Gln
    1235

<210> SEQ ID NO 17
<211> LENGTH: 216
<212> TYPE: PRT
<213> ORGANISM: artificial sequence
<220> FEATURE:
<223> OTHER INFORMATION: Rat IRS-1 fragment

<400> SEQUENCE: 17

Pro Pro Ala Arg Gly Glu Glu Leu Ser Asn Tyr Ile Cys Met Gly
1               5                   10                  15

Gly Lys Gly Ala Ser Thr Leu Thr Ala Pro Asn Gly His Tyr Ile Leu
            20                  25                  30

Ser Arg Gly Gly Asn Gly His Arg Tyr Ile Pro Gly Ala Thr Met Gly
        35                  40                  45

Thr Ser Pro Ala Leu Thr Gly Asp Glu Ala Ala Gly Ala Ala Asp Leu
    50                  55                  60

Asp Asn Arg Phe Arg Lys Arg Thr His Ser Ala Gly Thr Ser Pro Thr
65                  70                  75                  80

Ile Ser His Gln Lys Thr Pro Ser Gln Ser Ser Val Val Ser Ile Glu
                85                  90                  95

Glu Tyr Thr Glu Met Met Pro Ala Ala Tyr Pro Pro Gly Gly Gly Ser
            100                 105                 110

Gly Gly Arg Leu Pro Gly Tyr Arg His Ser Ala Phe Val Pro Thr His
        115                 120                 125

Ser Tyr Pro Glu Glu Gly Leu Glu Met His His Leu Glu Arg Arg Gly
    130                 135                 140

Gly His His Arg Pro Asp Ser Ser Asn Leu His Thr Asp Asp Gly Tyr
145                 150                 155                 160

Met Pro Met Ser Pro Gly Val Ala Pro Val Pro Ser Asn Arg Lys Gly
                165                 170                 175

Asn Gly Asp Tyr Met Pro Met Ser Pro Lys Ser Val Ser Ala Pro Gln
            180                 185                 190

Gln Ile Ile Asn Pro Ile Arg Arg His Pro Gln Arg Val Asp Pro Asn
        195                 200                 205

Gly Tyr Met Met Met Ser Pro Ser
```